United States Patent [19]

Barbachyn et al.

[11] Patent Number: 4,975,538

[45] Date of Patent: Dec. 4, 1990

[54] ANTIBIOTIC SULFONYLAMINOCARBONYL ACTIVATED BETA-LACTAMS

[75] Inventors: Michael R. Barbachyn, Kalamazoo; Steven J. Brickner, Portage; Richard C. Thomas, Oshtemo Township, Kalamazoo County, all of Mich.

[73] Assignee: The Upjohn Company, Kalamazoo, Mich.

[21] Appl. No.: 435,527
[22] PCT Filed: Feb. 19, 1988
[86] PCT No.: PCT/US88/00404
§ 371 Date: Aug. 25, 1989
§ 102(e) Date: Aug. 25, 1989
[87] PCT Pub. No.: WO88/06588
PCT Pub. Date: Sep. 7, 1988
[51] Int. Cl.$^5$ ............... A61K 31/64; C07D 401/14; C07D 413/14; C07D 205/085
[52] U.S. Cl. ...................... 540/363; 540/364
[58] Field of Search ........................ 540/363, 364

[56] References Cited

U.S. PATENT DOCUMENTS

| 4,587,047 | 5/1986 | Breuer | 260/239 A |
| 4,670,553 | 6/1987 | Breuer et al. | 540/363 |

FOREIGN PATENT DOCUMENTS

| 905502A | 1/1987 | Belgium. |
| 53815 | 12/1981 | European Pat. Off.. |
| 53816 | 12/1981 | European Pat. Off.. |
| 76758 | 10/1982 | European Pat. Off.. |
| 85291 | 10/1983 | European Pat. Off.. |
| 246786 | 11/1987 | European Pat. Off.. |
| 251143 | 1/1988 | European Pat. Off.. |
| 96297 | 12/1983 | Fed. Rep. of Germany. |
| 2181130 A | 4/1987 | United Kingdom. |

OTHER PUBLICATIONS

Breuer, H., et al., Abstract 371, Sept. 29–Oct. 2, 1985, XXV Interscience Conference on Antimicrobial Agents and Chemotherapy, Minneapolis, Minn.
Tanaka, S. K., et al., Abstract 372, Sept. 29–Oct. 2, 1985, XXV Interscience Conference on Antimicrobial Agents and Chemotherapy, Minneapolis, Minn.
Clark, J. M., et al., Abstract 373, Sept. 29–Oct. 2, 1985, XXV Interscience Conference on Antimicrobial Agents and Chemotherapy, Minneapolis, Minn.
Breuer, H. et al., Abstract 847, Sept. 28–Oct. 1, 1986, XXVI Interscience Conference on Amtimicrobial Agents and Chemotherapy, New Orleans, La.
Whitney, R. R., et al., Abstract 848, Sept. 28–Oct. 1, 1986, XXVI Interscience Conference on Antimicrobial Agents and Chemotherapy, New Orleans, La.
Pilkiewicz, F. G. and Remsburg, B. J., Abstract 849, Sept. 28–Oct. 1, 1986, XXVI Interscience Conference on Antimicrobial Agents and Chemotherapy, New Orleans, La.
Mochida, K. et al., Journal of Antibiotics, 182–189 (1987).

Primary Examiner—Mark L. Berch
Attorney, Agent, or Firm—Paul W. Busse; Donald L. Corneglio

[57] ABSTRACT

This invention presents novel 2-azetidinone compounds which are useful as antibacterial agents to eradicate or control susceptible microbes of the formula

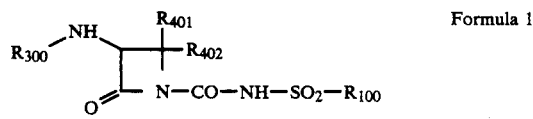

Formula 1 wherein $R_{401}$ and $R_{402}$ are the same or different and are (a) hydrogen, (b) ($C_1$–$C_{12}$) alkyl (c) ($C_2$–$C_8$) alkenyl, (d) ($C_2$–$C_8$) alkynyl, (e) ($C_3$–$C_{10}$) cycloalkyl, (f) phenyl optionally substituted with from one to 3 substituents selected from the group consisting of halogen, hydroxy, amino, nitro, ($C_1$–$C_4$) alkyl, and ($C_1$–$C_4$) alkoxy, (g) benzyl optionally substituted with from one to 3 substituents selected from the group consisting of halogen, hydroxy, amino, nitro, ($C_1$–$C_4$) alkyl, and ($C_1$–$C_4$) alkoxy, (h) $-CH_2-O-CO-CH_2-NHR_{420}$, (i) $-CH_2-O-CO_2-R_{430}$, (j) $-CH_2F$, or (k) $-CHF_2$; wherein $R_{420}$ is (a) hydrogen, (b) $-COH$, or (c) $-CO-O-C(CH_3)_3$; wherein $R_{430}$ is ($C_1$–$C_8$) alkyl, $-(CH_2)_2OC(O)NH_2$, $-(CH_2)_2Cl$, $-(CH_2)_2OCH_3$ or $-(CH_2)_2NHCOH$; wherein $R_{300}$ is an acyl group derived from a carboxylic acid; wherein $R_{100}$ is an optionally substituted heterocyclic moiety of Formula 2, 3, 4 or 5

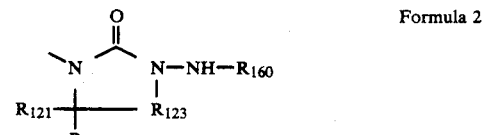

Formula 2

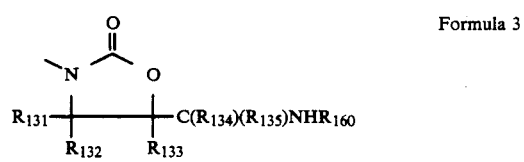

Formula 3

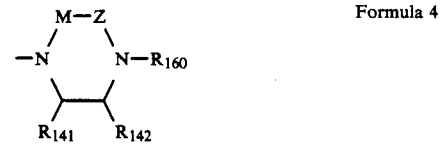

Formula 4

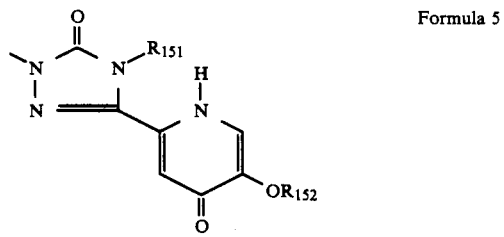

Formula 5

24 Claims, No Drawings

ANTIBIOTIC SULFONYLAMINOCARBONYL ACTIVATED BETA-LACTAMS

FIELD OF THE INVENTION

This invention encompasses novel antibiotic substituted sulfonylaminocarbonyl-2-azetidinones having a heterocyclic activating group.

INFORMATION DISCLOSURE

Derivatives of 2-azetidinone which have antimicrobial and $\beta$-lactamase inhibitory activity are known in the art. European Patent Application Nos. 0053815, 0053816 0076758, and 0096297 disclose $\beta$-lactams with various substituents at the $C_4$ position of the ring.

European Patent Application No. 0053816 discloses 2-azetidinone compounds substituted at the $C_4$ position with an organic residue However, the documents do not suggest the specific substituents disclosed herein and do not suggest or teach how to make the specific compounds of this application.

Abstracts from papers presented by Squibb Institute for Medical Research at the 25th and 26th Interscience Conferences on Antimicrobial Agents and Chemotherapy disclose antibacterial substituted sulfonylaminocarbonyl-2-azetidinones containing a substituted heterocycle in the sulfonylaminocarbonyl activating group at the N-1 position and a 2-(2-amino-4-thiazolyl)-2-(1-carboxy-1-methylethoxy)-iminoacetamido group at the $C_3$ position.

U.S. Pat. No. 4,587,047, filed Apr. 1, 1982, issued May 6, 1986 discloses substituted sulfonylaminocarbonyl-2-azetidinones. U.S. patent application Ser. No. 444,771 filed Nov. 26, 1982 and European Patent Application No. 0085291, filed Mar. 1, 1983, published Oct. 8, 1983 disclose substituted sulfonylaminocarbonyl-2-azetidinones containing a substituted heterocycle in the sulfonylaminocarbonyl activating group. U. K. Patent Application No. 8623151, filed Sept. 26, 1986 and Belgium Pat. No. 905502A disclose sulfonylaminocarbonyl-2-azetidinones containing an imidazolidonylaminocarbonyl-2-(1,4-dihydro-5-hydroxy-4-oxo)pyridine in the activating group. None of the above documents discloses a substituted sulfonylaminocarbonyl-2-azetidinone which has a heterocyclic activating group claimed in this invention.

Mochida, K., et al. Journal of Antibiotics, 182–189 (1987) disclose cephalosporins containing N-hydroxyl and N-methyl pyridinones and 5-hydroxypyridinones.

SUMMARY OF THE INVENTION

The present invention teaches novel 2-azetidinone analogs containing heterocyclic activating groups which are useful as microbial growth inhibitors. This invention includes enantiomers, diastereomeric and racemic mixtures of these compounds. Intermediates and processes for preparing these compounds are also disclosed.

Novel 2-azetidinone analogs within the scope of this invention are represented by Formula 1 and pharmaceutically acceptable salts thereof; wherein $R_{401}$ and $R_{402}$ are the same or different and are (a) hydrogen, (b) $(C_1-C_{12})$ alkyl (c) $(C_2-C_8)$ alkenyl, (d) $(C_2-C_8)$ alkynyl, (e) $(C_3-C_{10})$ cycloalkyl, (f) phenyl optionally substituted with from one to 3 substituents selected from the group consisting of halogen, hydroxy amino, nitro, $(C_1-C_4)$alkyl, and $(C_1-C_4)$alkoxy, (g) benzyl optionally substituted with from one to 3 substituents selected from the group consisting of halogen, hydroxy, amino, nitro, $(C_1-C_4)$alkyl, and $(C_1-C_4)$alkoxy, (h) —CH$_2$—O—CO—CH$_2$—NHR$_{420}$, (i) —CH$_2$—O—CO$_2$—R$_{430}$, (j) —CH$_2$F, or (k) —CHF$_2$; wherein $R_{420}$ is (a) hydrogen, (b) —COH, or (c) —CO—O—C(CH$_3$)$_3$; wherein $R_{430}$ is $(C_1-C_8)$alkyl, —(CH$_2$)$_2$OC(O)NH$_2$, —(CH$_2$)$_2$Cl, —(CH$_2$)$_2$OCH$_3$ or —(CH$_2$)$_2$NHCOH; wherein $R_{300}$ is an acyl group derived from a carboxylic acid; wherein $R_{100}$ is a heterocyclic compound of Formulas 2, 3, 4 or 5; wherein $R_{121}$ and $R_{122}$ are hydrogen; wherein $R_{123}$ is methylene or carbonyl; wherein $R_{131}$ and $R_{132}$ are hydrogen or $(C_1-C_3)$ alkyl with the proviso that if one of $R_{131}$ or $R_{132}$ is alkyl the other is hydrogen; wherein $R_{133}$, $R_{134}$ and $R_{135}$ are the same or different and are (a) hydrogen, (b) $(C_1-C_3)$ alkyl, (c) $(C_3-C_4)$ cycloalkyl, or (d) phenyl with the proviso that if one of $R_{134}$ or $R_{135}$ are $(C_1-C_3)$ alkyl, $(C_3-C_4)$ cycloalkyl, or phenyl the other is hydrogen; wherein $R_{141}$ and $R_{142}$ are the same or different and are (a) hydrogen, (b) $(C_1-C_4)$ alkyl, (c) $(C_2-C_3)$ alkenyl, (d) $(C_3-C_6)$ cycloalkyl, or (e) phenyl; wherein groups b, c, d and e may be substituted by one to 2 substituents selected from the group consisting of halogen, hydroxy, amino, nitro, $(C_1-C_4)$alkyl, and $(C_1-C_4)$alkoxy; wherein M is carbonyl or methylene; wherein Z is NH or C(R$_{143}$)(R$_{144}$); wherein $R_{143}$ and $R_{144}$ are the same or different and are (a) hydrogen, (b) $(C_1-C_4)$ alkyl, (c) $(C_2-C_3)$ alkenyl, (d) $(C_3-C_6)$ cycloalkyl, or (e) phenyl; wherein $R_{151}$ is (a) hydrogen, (b) $(C_1-C_4)$ alkyl, (c) $(C_3-C_6)$ cycloalkyl, (d) phenyl, or (e) —CF$_3$; wherein groups b, c and d may be substituted by one to 2 substituents selected from the group consisting of halogen, hydroxy, amino, nitro, $(C_1-C_4)$alkyl, and $(C_1-C_4)$; and wherein $R_{152}$ is hydrogen or- CH$_2$(C$_6$H$_5$); wherein $R_{160}$ is a pyridinone of Formulas 6, 7, 8, 9 or 10; wherein $L_1$ is (a) hydrogen, (b) $(C_1-C_4)$ alkyl, (c) $(C_2-C_3)$ alkenyl, (d) $(C_3-C_6)$ cycloalkyl, (e) phenyl, or (f) —CF$_3$; wherein groups b, c d and e may be substituted by one to 2 substituents selected from the group consisting of halogen, hydroxy, amino, nitro, $(C_1-C_4)$alkyl, and $(C_1-C_4)$alkoxy; wherein $L_2$ is hydrogen or —CH$_2$(C$_6$H$_5$); and wherein $L_{161}$ is carbonyl; with the proviso that when $R_{160}$ is of Formula 6 and where $R_{121}$ and $R_{122}$ are hydrogen and $R_{123}$ is methylene, $L_1$ and $L_2$ are not hydrogen.

A detailed description of the acyl groups included in $R_{300}$ is found in U.S. Pat. No. 4,478,749, column 8, line 41 to column 12, line 50, as those terms are defined at column 7, line 34 through column 8, line 22, all of which is incorporated by reference herein.

Preferred acyl groups of $R_{300}$ include those which have been used to acylate 6-aminopenicillanic acid, 7-aminocephalosporic acid and their derivatives which can be found in "Chemistry and Biology of $\beta$-Lactam Antibiotics", Vol. 1, R. B. Morin and M. Gorham, ed., Academic Press, N.Y. 1982 and include the following list: 2-Cyanoacetyl, A-minophenylacetyl, Amino(4-hydroxyphenyl)acetyl, $\alpha$(Thien-2-yl)acetyl, $\alpha$(Thien-3-yl)acetyl, Phenylacetyl, Hydroxyphenylacetyl, (Formyloxy)-phenylacetyl, [(Trifluoromethyl)thio]acetyl, 2-(3,5-Dichloro-4-oxo-1-(4H)-pyridyl)acetyl (1H-Tetrazol-1-yl)acetyl, (2-Amino-4-thiazolyl)-2-methoxyiminoacetyl, 2-[(Cyanomethyl)thio]acetyl, [[(4-Ethyl-2,3-dioxo-1-piperizinyl)carbonyl]amino]phenylacetyl, [[(4-Ethyl-2,3-dioxo-piperazinyl)carbonyl]amino](4-hydroxyphenyl)acetyl, 2-(Aminomethyl)phenylacetyl, 4-(Carbamoylcarboxymethylene)-1,3-dithiethane-2-carbonyl, 3-(o-Chlorophenyl)-5-methyl-4-isoxazolecarbonyl, 2-p-[(1,4,5,6-Tetrahydro-2-pyrimidinyl)phenyl]acetyl, Amino-1,4-cyclohexadien-1-yl-acetyl, Phenylsulfoacetyl, (2R)-2-amino-2-(m-methanesulfonamidophenyl)acetyl, (2-Amino-4-thiazolyl)-2-(1-carboxy-1-methylethoxy)iminoacetyl, 2-(1H-Tetrazol-1-yl)acetyl, (2,3-Dihydro-2-imino-4-thiazolyl)(methoxyimino)acetyl, (2-Amino-4-thiazol)carboxymethoxyiminoacetyl, (2-Aminopyridin-6-yl)methoxyiminoacetyl, (2-Aminopyridin-6-yl)carboxymethoxyiminoacetyl, (4-Amino-2-pyrimidyl)methoxyiminoacetyl, (5-Amino-1,2,4-thiadiazol-3-yl)-2-methoxyiminoacetyl, (5-Amino-1,2,4-thiadiazol-3-yl)-2-carboxymethoxyiminoacetyl, (5-Amino-1,2,4-thiadiazol-3-yl)-1-carboxy-1-methylethoxy)iminoacetyl, D,α[[(Imidazolidin-2-on-1-yl)-carbonyl]amino]phenylacetyl, D,α[[(3-mesyl-imidazolidin-2-on-1-yl)carbonyl]amino]phenylacetyl, 2,6-Dimethylbenzoyl, (S)-2-(4-hydroxy-1,5-naphthyridine-3-carboxamido-2-phenylacetyl.

Preferred compounds within the scope of this invention include compounds wherein the organic acid derivative, $R_{300}$, is an oximinoacyl moiety represented by Formula 11; wherein $R_{320}$ is (a) —$CH_3$, (b) —$CH_2CO_2R_{321}$, (c) —$C(CH_3)_2CO_2R_{321}$, (d) —$CH(CH_3)CO_2R_{321}$, (e) —$C(CH_2)$—$CO_2R_{321}$, (f) —$X$—$CO_2R_{321}$, (g) —$CH_2CONHOH$, or (h) —$C(CH_3)_2CONHOH$; wherein X is 1,1-cyclopropyl, 1,1-cyclobutyl, or 1,1-cyclopentyl; wherein $R_{321}$ is (a) hydrogen, (b) ($C_1$–$C_4$) alkyl, (c) —$CH(C_6H_5)_2$, (d) —$CH_2(C_6H_5)$, or (e) a cation; wherein $R_{330}$ is (a) hydrogen, (b) —$CO$—$O$—$C(CH_3)_3$, (c) —$CO$—$O$—$CH_2$—$(C_6H_5)$, or (d) —$C(C_6H_5)_3$.

Novel compounds within the scope of this invention containing an oximinoacyl moiety represented by Formula 11 which are useful as intermediates to 2-azetidinone analogs having microbial growth inhibition include compounds wherein $R_{321}$ is ($C_1$–$C_4$) alkyl, —$CH$—$(C_6H_5)_2$, or —$CH_2(C_6H_5)$; and wherein $R_{330}$ is —$CO$—$O$—$C(CH_3)_3$, —$CO$—$O$—$CH_2$—$(C_6H_5)$, or —$C(C_6H_5)_3$.

The compounds of this invention are identified in several ways: by the Chemical Abstract name, by descriptive chemical name, and by numerical identification which corresponds to the appropriate structure contained in the structure charts. In appropriate situations, the proper stereochemistry is represented in the structure charts as well.

The various carbon moieties are defined as follows: Alkyl refers to an aliphatic hydrocarbon radical and includes branched or unbranched forms such as methyl, ethyl, n-propyl, isopropyl n-butyl, isobutyl, sec-butyl, t-butyl, n-pentyl, isopentyl, neo-pentyl, n-hexyl, isohexyl, n-heptyl isoheptyl, n-octyl isooctyl, n-nonyl, n-decyl, n-undecyl, and n-dodecyl; Alkoxy refers to an alkyl radical which is attached to the remainder of the molecule by oxygen and includes branched or unbranched forms such as methoxy, ethoxy, n-propoxy, isopropoxy, n-butoxy isobutoxy, sec-butoxy, and t-butoxy; Alkenyl refers to a radical of an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl; Alkynyl refers to a radical of an aliphatic unsaturated hydrocarbons having a triple bond and includes both branched and unbranched forms such as ethynyl, 1-methyl-1-ethynyl, 1-propynyl, 2-propynyl, 1-butynyl, 2-butynyl, 3-butynyl, 2-methyl-1-butynyl, 1-pentynyl, 2-pentynyl, 3-pentynyl, 4-pentynyl, 1-methyl-4-pentynyl, 3-methyl-1-pentynyl, 3-methyl-2-pentynyl, 1-hexynyl, 2-hexynyl, 3-hexynyl, 4-hexynyl, 1-methyl-4-hexynyl, 3-methyl-1-hexynyl, 3-methyl-2-hexynyl, 1-heptynyl, 2-heptynyl, 3-heptynyl, 4-heptynyl, 1-methyl-4-heptynyl, 3-methyl-1-heptynyl, 3-methyl-2-heptynyl, 1-octynyl, 2-octynyl, or 3-octynyl.

Aryl refers to a radical derived from an aromatic hydrocarbon atom such as phenyl, methylphenyl, dimethylphenyl, α-naphthyl, β-naphthyl, biphenyl, or anthryl.

Cycloalkyl refers to a radical of a saturated cyclic hydrocarbon such as cyclopropyl, cyclobutyl, cyclopentyl, cyclohexyl, cycloheptyl, cyclooctyl or adamantyl.

Halogen refers to a radical of fluorine, chlorine, bromine, or iodine.

Heterocyclic radical refers to a 5 to 8 atom heterocyclic ring or fused rings having between one and 4 heteroatoms in the ring such as nitrogen, oxygen and sulfur. Examples of heterocyclic radicals are 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, 2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3-, or 5-(1,2,4-oxadiazolyl), 1,3,4-oxadiazolyl, 1,2,5-oxadiazolyl, 1,2,3-or 1 2,4-triazolyl, 1H- or 2H-tetrazolyl, pyrido[2,3-d]pyrimidyl, benzopyranyl, 1,8-, 1,5-, 1,6-, 1,7- 2,7- or 2,6-naphthyridyl, quinolyl, or thieno[2,3-b]pyridyl, Unless otherwise indicated, in the above description and throughout this document: (a) the parenthetical term ($C_n$–$C_m$) is inclusive such that a compound of ($C_1$–$C_4$) would include compounds of 1, 2, 3 and 4 carbons and their isomeric forms; (b) in substituents specifying carbonyl such as ($C_2$–$C_4$)alkylcarbonyl, the prefix ($C_2$–$C_4$) includes the carbonyl carbon limiting the total number of carbons in the alkyl to no more than 4; and, (c) where two multiple carbon moieties are present on a substituent such as ($C_2$–$C_4$)alkoxyalkyl, the total number of carbon atoms does not exceed 4.

It will be apparent to those skilled in the art that compounds of this invention may exist in different tautomeric forms. The scope of this invention includes all tautomeric forms in addition to those represented in the formulas used herein.

It will be apparent to those skilled in the art that compounds of this invention may contain several chiral centers. The scope of this invention includes all enantiomeric or diastereomeric forms of Formula 1 compounds either in pure form or as mixtures of enantiomers or diastereomers. Specifically, the azetidinones of this invention have chiral carbon atoms at positions $C_3$ and $C_4$ of the β-lactam ring. The preferred form is cis at centers 3 and 4 and the preferred stereochemistry at $C_3$ and $C_4$ is 3(S) and 4(S). The phrase "cis at centers 3 and 4"

means that the substituents at C-3 and C-4 are both oriented on the same side of the β-lactam ring.

The scope of this invention includes the pharmaceutically acceptable acid salts of the disclosed compounds. Acid salts are formed by reacting the compounds described herein with the appropriate acid in a suitable solvent. Suitable acids for this purpose include hydrochloric, sulfuric, phosphoric, hydrobromic, hydroiodic, acetic, lactic, citric, succinic, benzoic, salicylic, palmoic, cyclohexansulfamic, methanesulfonic, naphthalenesulfonic, p-toluenesulfonic, maleic, fumaric, or oxalic.

The scope of this invention includes the pharmaceutically acceptable salts of the disclosed compounds. Such salts include the following cations but are not limited to these: alkali metal ions such as potassium, sodium, lithium, alkaline earth metal ions such as magnesium or calcium and ammonium ions such as ammonium, tetralkylammonium and pyridinium. Metal salts are formed by suspending the compounds in water or other suitable solvent and adding a dilute metal base such as sodium or potassium bicarbonate until the pH is between 6 and 7.

The compounds of this invention and their respective pharmaceutically acceptable salts have antibiotic activity against a variety of gram-negative bacteria including *Escherichia coli, Klebsiella pneumoniae,* and *Pseudomonas aeruginosa.* The compounds are useful for treating bacterial infections in animals, including and most preferably humans. Compounds of the invention are tested for in vitro antimicrobial activity using standard testing procedures such as the determination of minimum inhibitory concentration (MIC) by methods described in "Methods for Dilution Antimicrobial Susceptibility Tests for Bacteria That Grow Aerobically" (M7-A) Published December 1985 by the National Committee for Clinical Laboratory Standards, 771 East Lancaster Avenue, Villanova, Pa. 19084. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Tryptiease Soy Broth (TSB) until a turbidity of 0.5 McFarland standard is obtained. The bacteria are diluted one to twenty in TSB and inoculated on the plates (1 μl using a Steers replicator). The plates are incubated at 35° C. for 20 hours and the MIC is read to be the lowest concentration of drug that completely inhibits visible growth of the bacterium. Representative MIC test results for several typical compounds of this invention are given in Table I.

Various compositions of the present invention are presented for administration to humans and animals in unit dosage forms, such as tablets, capsules, pills, powders, granules, sterile parenteral solutions or suspensions, eye drops, solutions or suspensions, and emulsions containing suitable quantities of compounds of Formula 1.

For oral administration solid or fluid unit dosage forms can be prepared. For preparing solid compositions, the compounds of this invention are mixed with conventional ingredients such as talc, magnesium stearate, dicalcium phosphate, magnesium aluminum silicate, calcium sulfate, starch, lactose, acacia, methylcellulose, and/or functionally similar pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

For preparing fluid compositions the compounds of this invention are dissolved in an aqueous vehicle together with sugar, aromatic flavoring agents and preservatives to form a syrup. An elixir is prepared by using a hydroalcoholic vehicle such as ethanol, suitable sweeteners such as sugar and saccharin, and aromatic flavoring agents. Suspensions are prepared in an aqueous vehicle with the aid of a suspending agent such as acacia, tragacanth, or methylcellulose.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compounds of Formula 1 may also be administered in a carrier suitable for topical administration, such carriers include creams, ointments, lotions, pastes, jellies, sprays, aerosols, bath oils, or other pharmaceutical carriers which accomplish direct contact between the compound and the surface of the skin area to be treated. In general pharmaceutical preparations may comprise from about 0.01% to about 10%, and preferably from about 0.1% to about 5% by w/w of the active compound in the suitable carrier.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 g.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on the unique characteristics of the active material and the particular effect to be achieved and the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, drops, ampules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans having an average weight of 70 kg is from about 50 to about 3000 mg of compound in a single dose. More specifically, the single dose is from about 100 mg to 2000 mg of compound. Typically the dosages are given one to 4 times per day.

The process for making compounds of Formula 1 is illustrated in Charts A and B. The requirements for protecting groups in the processes of Charts A and B are well recognized by one skilled in the art of organic chemical synthesis and suitable protecting groups are used in the processes of Charts A and B. It is recognized that conditions for introduction and removal of protecting groups should not detrimentally alter any other groups in the molecule. Examples of suitable nitrogen protecting groups are: (1) benzyl; (2) triphenylmethyl (trityl); (3) trialkylsilyl, such as trimethylsilyl or t-butyldimethylsilyl; (4) t-butoxycarbonyl (t-BOC or BOC); (5) benzyloxycarbonyl (Cbz); (6) trifluoroalkanoyl, such as trifluoroacetyl or trifluoropropionyl; or (7) diphenyl(methyl)silyl.

Introduction and removal of such nitrogen protecting groups are well known in the art of organic chemistry: See, for example, (1) J. F. W. McOmie, Advances in Organic Chemistry, 3:191–281 (1963); (2) R. A. Boissonas, Advances in Organic Chemistry, 3:159–190 (1963); (3) "Protective Groups in Organic Chemistry", J. F. W. McOmie, Ed., Plenum Press, New York, 1973, p, 74, and (4) "Protective Groups in Organic Synthesis", Theodora W. Greene, John Wiley and Sons, New York, 1981.

Under certain circumstances it may be necessary to protect two or more nitrogen atoms with different protecting groups allowing selective removal of one protecting group while leaving the remaining protecting groups in place. For example, the Cbz group can be selectively removed in the presence of the BOC group and vice versa.

The compounds of this invention are prepared by the procedures outlined in Charts A and B. The substituents at the $C_4$ position defined by $R_{401}$ and $R_{402}$ are prepared by procedures outlined in Chart A. The starting compound cis-($\pm$)-4-(methoxycarbonyl)-3-[[(benzyloxy)carbonyl]amino]-2-azetidinone, A-1, is known. See J. Org. Chem., 2765–2767 (1982). The trans compound is known or is made by known methods. Thus compound A-1 is either cis or trans with respect to the substituents on $C_3$ and $C_4$. It is recognized that alternative protecting groups could be used in place of the benzyloxycarbonyl group of compound A-1. See also, W. F. Huffman et al., J. Am. Chem Soc., 2352 (1977); D. B. Bryan et al., J. Am. Chem. Soc., 2353 (1977).

The $C_4$-carbomethoxy group of compound, A-1, is reduced to the $C_4$-hydroxymethyl group of compound, A-2, by use of metal hydride reducing reagents, such as sodium borohydride or zinc borohydride, in ether solvents, such as diethyl ether or tetrahydrofuran, at a temperature range of 0° to 80° C. The product is obtained after a normal aqueous work-up procedure followed by column chromatography on silica gel.

The hydroxymethyl group of compound, A-2, reacts with $HO_2CCH_2$—$NHR_{420}$, wherein $R_{420}$ is —COH or —BOC, to produce compound A-4 using approximately equimolar quantities of the acid, 1-hydroxy-1-benzotriazole (HOBT), and a carbodiimide, such as dicyclohexylcarbodiimide (DCC) and a catalytic amount of 4-dimethylaminopyridine. The choice of solvents is methylene dichloride, dimethylformamide or a combination of both solvents and the reaction is carried out in general at the temperature range of 0° C. to ambient temperature. The desired compound is obtained after filtration of precipitated dicyclohexylurea and removal of HOBT by washing with aqueous sodium bicarbonate solution and then column chromatography on silica gel.

To prepare compounds represented by A-3, the hydroxymethyl compound, A-2, reacts with a suitable protected chloroformate ester of formula $ClCO_2R_{430}$ where $R_{430}$ is $(C_1-C_8)$ alkyl, —$(CH_2)_2OC(O)NH_2$, —$(CH_2)_2Cl$, —$(CH_2)_2OCH_3$ or —$(CH_2)_2NHC(O)H$, to give the compound, A-3. The reaction conditions involve the use of an inert solvent such as methylene dichloride, tetrahydrofuran, or dimethylformamide at $-20°$ C. to 30° C. in the presence of a slight excess of organic base, such as pyridine, 2,4-lutidine, or triethylamine. Following extractive workups involving successive washes with acid and base, the products are isolated by chromatography or crystallization. Some chloroformate esters are commercially available and others are be prepared according to the teaching of Huntress, "Organic Chlorine Compounds," John Wiley and Sons, Inc., New York, N.Y., 1948; F. Stain et al., J. Am. Chem. Soc., 72, 1254 (1950), H, G, Ashburn, et al., J. Am. Chem. Soc., 60, 2933 (1938). Briefly, the process described in these references is to contact an alcohol with an excess of phosgene either neat or in an organic solvent. After workup, the product is usually isolated by vacuum distillation.

An alternative process to prepare compounds represented by A-3, can be used when the desired chloroformate is unavailable. Compound A-2 is placed in a solvent such as methylene dichloride, ethyl acetate, tetrahydrofuran, or acetonitrile containing a slight excess of an organic base, such as pyridine, triethylamine, or 2,4-lutidine, and is reacted at $-20°$ C. to 30° C. with a solution of phosgene in an inert solvent, such as toluene, benzene or methylene dichloride. The intermediate chloroformate thus formed is not isolated, but is treated with a molar equivalent of the suitably protected desired alcohol, $R_{430}OH$, where $R_{430}$ is $(C_1-C_8)$ alkyl, —$(CH_2)_2OC(O)NH_2$, —$(CH_2)_2Cl$, $(CH_2)_2OCH_3$ or —$(CH_2)_2NHCOH$, in the presence of an organic base in an inert solvent at $-20°$ C. to 30° C. to yield the compound, A-3. This alternative or reversed process is known in the field of steroid chemistry, G. Schubert, et al., Die Pharmazie, 35:453 (1980).

To prepare compounds of this invention wherein $R_{401}$ or $R_{402}$ are alkyl, alkenyl, alkynyl, cycloalkyl, optionally substituted phenyl or benzyl or fluoroalkyl, the hydroxyl substituent in compound A-2 is converted to an appropriate leaving group, Lg, by methods known in the art to give compound, A-5. The leaving group is displaced by a known nucleophiles by methods known in the art to give compound A-6 wherein R' is alkyl, alkenyl, alkynyl, cycloalkyl, optionally substituted phenyl or benzyl or fluoroalkyl.

To prepare compounds of this invention wherein $R_{401}$ or $R_{402}$ are the same, a suitable amino acid derivative, A-7, is cyclized by known methods to give the substituted four membered ring, A-8, Slusarchyk, W. A., et al., Tetrahedron Letters, 2789–2792 (1986). Deprotection of the lactam nitrogen gives the hydroxy amide, A-9, which is reduced to the $\beta$-lactam by titanium trichloride in tetrahydrofuran and water, Miller, M. J., et al, J. Org. Chem., 1126 (1985), Miller, M. J., et al., J. Org. Chem., 410 (1980), Miller, M. J., et al., Tetrahedron, 2571 (1983). Other procedures to prepare substituted azetidinones are known in the art; see, for example, Teutsch, G., et al., Tetrahedron, 2677–2684 (1986), Teutsch, G., et al., Tetrahedron Letters, 1561–1562 (1984), and U.S. Pat. No. 4,478,749, column 19, lines 1–40.

Optically active compounds of the Formula 1 of this invention are prepared by the use of the appropriate optically active form of compound, A-1, which is prepared by known methods, Takeda European patent application No. 8310461-3. The resolving agents are any of the known resolving agents such as optically active camphorsulfonic acid, bis-o-toluoyltartaric acid, tartaric acid, and diacetyl tartaric acid which are commercially available and which are commonly used for resolution of amines. See Organic Synthesis, Coll. V:932 (1978), which describes the resolution of R-(+) and S-(−)-α-phenylethylamine with (−)-tartaric acid.

The preferred starting compound for making optically active compounds of Formula 1, cis-($\pm$)-1-[(2',4'-dimethoxyphenyl)methyl]-4-methoxycarbornyl)-3-phenylmethoxycarboxyamino-2-azetidinone, is known, Chem. Pharm. Bull., 2646–2659 (1984). The $C_3$ protecting group is removed by hydrogenolysis to produce the corresponding free amine. An appropriate substituted tartaric acid enantiomer is then added such as (+)-di-p-toluoyl-D-tartaric acid and reaction conditions altered to facilitate precipitation of the appropriate azetidinone diastereomeric salt. The tartaric acid is removed by treating the compound with inorganic base such as aqueous sodium bicarbonate to produce the desired resolved amino-azetidinone.

Alternative procedures to prepare the nitrogen heterocyclic portion of the compounds of this invention represented by Formula 2 are shown in Chart C. One method for the preparation of the compound condenses a suitable amino acid, C-1, with t-butyl carbazate which cyclizes directly to the hydantoin, C-2, Lalezari T., et al., J. Heterocyclic Chem., 741 (1985). Another method uses a stepwise process which condenses an amino ester, C-3, with ethyl chloroformate to give, C-4, which reacts with hydrazine in ethanol to give the diazocarbamate, C-5. The diazocarbamate, C-5, cyclizes in DMF to give the desired hydantoin, C-2, Schlogl, K., et al., Monatsh. Chem., 607 (1954).

Alternative synthesis to prepare the nitrogen heterocyclic portion of the compounds of this invention represented by Formula 3 are shown in Chart C using methods known in the art. To prepare compounds wherein $R_{131}$ and $R_{132}$ are hydrogen or $(C_1-C_3)$ alkyl, the appropriately 3,3-disubstituted-1-chloro-2-propene, C-10, is epoxidized by known reagents, such as m-chloroperbenzoic acid, in a inert solvent to give compound C-11. Solvolytic epoxide ring opening in the presence of isocyanate generates an intermediate $\beta$-substituted alcohol which readily ring closes to give the substituted chlorooxazolidinone, C-12. The chloro-oxazolidinone reacts with sodium azide in an inert solvent to give the azide which is reduced by known methods, such as hydrogen gas in the presence of palladium, to give the amino compound, C-13. An analogous procedure is used to prepare compounds wherein $R_{134}$ and $R_{135}$ are hydrogen, $(C_1-C_3)$ alkyl, $(C_3-C_4)$ cycloalkyl or phenyl by using an appropriate 1,1-disubstituted-1-chloro-2-propene as the starting alkene. The order of synthetic steps in the above procedure may be changed to accommodate certain substrates. For example, the chloride in the starting alkene is aminated using the azide/reduction procedure described. The amine is protected with a suitable known protecting group and the rest of the synthetic sequence, epoxidation, isocyanate ring opening and ring closure, is completed. Removal of the protecting group gives the amino compound, C-13.

The procedure used to prepare compounds represented by Formula 3 wherein $R_{133}$ is hydrogen, $(C_1-C_3)$ alkyl, $(C_1-C_3)$ cycloalkyl, or phenyl is also outlined in Chart C. The protected aminoketone, C-14, reacts with known reagents to give the cyanohydrin, C-15. The cyano compound is reduced to the amine with borane in an inert solvent to give the aminohydroxy compound, C-16, which condenses with dichloro or diethyl carbonate to give the protected amino-oxazolidinone, C-17. Removal of the protecting group gives the amino compound, C-18. An alternative procedure to prepare compounds wherein $R_{133}$ is hydrogen, $(C_1-C_3)$ alkyl, $(C_3-C_4)$ cycloalkyl or phenyl uses the dicyano compound, C-19, which reacts with known reagents to give the di-cyanohydroxy compound, C-20. Compound C-20 reacts with an excess of borane in an inert solvent to give the di-aminohydroxy compound, C-21, which is converted to the amino-oxazolidinone, C-18, through the carbonate condensation reaction described above.

The nitrogen heterocyclic portion of the compounds of this invention represented by Formula 4 wherein M is methylene are commercially available or are prepared by methods known in the art. Substituted compounds of Formula 4 wherein M is carbonyl are prepared according to procedures described below. To prepare compounds wherein Z is $C(R_{143})(R_{144})$, ethylene diamine and a suitable disubstituted α-halogen ester are condensed in a suitable solvent as described in Aspinall, S, R., J, Amer, Chem. Soc, 1202–1204 (1940). When an appropriately substituted ethylene diamine is used in this procedure, compounds wherein $R_{141}$ and $R_{142}$ are the same or different and are hydrogen, $(C_1-C_4)$ alkyl, $(C_2-C_3)$ alkenyl, $(C_3-C_6)$ cycloalkyl, phenyl, or substituted derivatives thereof, are prepared. Substituted ethylene diamines are commercially available or prepared by methods known in the art. Substituted compounds of Formula 4 wherein Z is NH, are prepared from an appropriately substituted aminoimidazolidinones, C-30, which upon heating ring expands to the compound, C-31. Appropriately substituted aminoimidazolidinones are prepared by condensing substituted ethylene diamines, which are commercially available or prepared by methods known in the art, with an activated carbonate, such as dichlorocarbonate, which gives the imidazolidinone. The imidazolidinone reacts with nitrous acid to from the nitroso-imidazolidinone which is reduced to the amine by methods known in the art.

The procedure used to prepare the nitrogen heterocyclic portion of the compounds of this invention represented by Formula 5 is also outlined in Chart C. A commercially available semicarbazide or a semicarbazide readily prepared by known methods, C-40, where $R_{151}$ is hydrogen, $(C_1-C_4)$ alkyl, $(C_3-C_6)$ cycloalkyl, phenyl, or $-CF_3$, or substituted derivatives thereof, is condensed with the pyridone carboxylic acid, C-41, where $R_{152}$ is $-CH_2(C_6H_5)$ in a suitable solvent, such as DMF, in the presence of DCC, HOBT and an amine base, such as 4-dimethylaminopyridine or triethylamine to give C-42. The condensed compound, C-42, cyclizes when heated in the presence of base, such as aqueous potassium hydroxide to give the substituted compound, C-43.

Pyridinones represented by Formula 6 are prepared from the pyranone acid, C-51 in Chart C, by reacting the pyranone acid with ammonium hydroxide or a primary amine, $H_2NL1$, where $L_1$ is hydrogen, $(C_1-C_4)$ alkyl, $(C_2-C_3)$ alkenyl, $(C_3-C_6)$ cycloalkyl, phenyl, or $-CF_3$; or substituted derivatives thereof with or without a suitable solvent such as water, THF or DMF to give compounds represented by Formula 6, where $L_2$ is $-CH_2-(C_6H_5)$ and $R_{161}$ is $-CO_2H$. The pyridinone acid is purified by column chromatography, recrystallization or methods known to those skilled in the art.

Pyridinones represented by Formula 7 are prepared from pyranone C-50 in Chart C, where $R_{51}$ is hydrogen and $R_{52}$ is $CH_2-O-CO(C_6H_5)$. Compound C-50 reacts with phenyldiazomethane in chloroform and diethyl ether to give the benzylated derivative, where $R_{51}$ is $CH_2-(C_6H_5)$. The benzoyloxy group is selectively removed in the presence of sodium methoxide in methanol and then reacts with Jones reagent in acetone to give the pyranone acid, where $R_{52}$ is $C_2OH$. The pyranone acid reacts with ammonium hydroxide or a primary amine, $H_2NL1$, where $L_1$ is hydrogen $(C_1-C_4)$ alkyl, $(C_2-C_3)$ alkenyl, $(C_3-C_6)$ cycloalkyl, phenyl, or $-CF_3$; or substituted derivatives thereof in a suitable solvent, such as water, THF or DMF to give compounds represented by Formula 7, where $L_2$ is $-CH_2-(C_6H_5)$ and $R_{161}$ is $CO_2H$. The pyridinone acid is purified by column chromatography, recrystallization or methods known to those skilled in the art.

The pyranone, C-50, is prepared from 1-O-methyl-α-D-galactopyranoside according to the method described by Lichtenthaler, F. W., et al., Chem, Ber., 110, 3324–3332 (1977).

Pyridinones represented by Formulas 8 and 10 are prepared from 2,6-dibromopyridine and 2,4 dibromopyridine, C-52a or C-52b in Chart C. The dibromopyridine is lithiated with one equivalent of n-butyl lithium in THF in the cold and reacted with carbon dioxide to give the bromoacid after work up. The bromoacid reacts with hydrogen peroxide in trifluoroacetic acid to give the N-oxide which is converted to the hydroxyl amine with aqueous potassium hydroxide.

Pyridinones represented by Formula 9 are prepared from 2-amino-4-methylpyridine, C-53 in Chart C. The amino group is converted to the bromide and the methyl group is oxidized to the carboxylic acid by methods known in the art. The bromide reacts with hydrogen peroxide in trifluoroacetic acid to give the N-oxide which is converted to the hydroxyl amine with aqueous potassium hydroxide.

The heterocyclic fragment of the compounds represented by Formulas 2, 3 and 4 are coupled to a protected pyridinone carboxylic acid, C-60, C-61, C-62, C-63, or 64; where $L_1$ is hydrogen, $(C_1-C_4)$ alkyl, $(C_2-C_3)$ alkenyl, $(C_3-C_6)$ cycloalkyl, phenyl, or $-CF_3$; or substituted derivatives thereof. The coupling reaction is done in a suitable solvent, such as DMF, in the presence of HOBT and DCC or DIC at ambient temperatures. The coupled products, C-65, C-66, or C-67, are purified by column chromatography, recrystallization or methods known to those skilled in the art.

Alternative procedures to complete the rest of the molecule are outlined in Chart B. As shown in Chart B, the benzyloxycarbonyl group of compound B-1, is removed by catalytic hydrogenolysis using palladium metal supported on carbon or palladium metal itself under a hydrogen gas atmosphere in suitable solvents, such as alcoholic solvents, ether solvents or ethyl acetate, at ambient temperature. The compound, B-2, is obtained by removal of the solid catalyst and removal of the solvent under reduced pressure.

The $C_3$-amino group of compound, B-2, is acylated with a suitable carboxylic acid to produce compound, B-3. This conversion may be carried out by any of a number of amide or peptide forming reaction sequences such as methods described in Methoden der Organischem Chemie, Vierte Auflage, Band XV/2, E. Wunch ed., Georg Thieme Verlag, Stuttgart, page 1. A preferred acylation process is the use of approximately equimolar quantities of a desired acid, HOBT, and a carbodiimide, such as DCC or DIC. The choice of solvents is methylene dichloride, dimethylformamide or a combination of both solvents and the reaction is carried out in general at the temperature range of 0° C. to ambient temperature. The desired compound is obtained after filtration of precipitated dicyclohexylurea, removal of HOBT by washing with aqueous sodium bicarbonate solution and column chromatography on silica gel if necessary. Also, the compounds can be made by other methods known in the art, see, for example, J. Am. Chem. Soc., 2401–2404 (1973).

The amide, B-3, reacts with approximately 1.2 to 1.6 equivalents of chlorosulfonyl isocyanate at −20° to 0° C. in organic solvents, such as methylene dichloride, acetonitrile or a combination of both solvents to produce the activated azetidinone B-4 which is coupled to a silylated intermediate prepared by reacting N-methyl-N-(trimethylsilyl)-trifluoroacetamide or bis-(trimethylsilyl)-trifluoroacetamide with a suitable heterocycle compound of Formula 2, 3 or 4 in organic solvents, such as acetonitrile, methylene dichloride or tetrahydrofuran, at ambient temperature. The silylated intermediate reacts with compound B-4 optionally in the presence of a tertiary amine base such as 2,6-lutidine at about 0° C., and the mixture is stirred at 0° or slowly warmed to room temperature over a period of one to 5 hours. The crude product is obtained after a normal aqueous work-up procedure and followed by purification by column chromatography. Removal of any remaining protecting groups by known methods gives the N-1-sulfonyl-aminocarbonyl compound, B-5.

Alternatively, following the procedure outlined in Chart B, a methylene chloride solution of the B-1 and 2,6-lutidine reacts with chlorosulfonyl isocyanate at 0° to give B-6. B-6 reacts with an acetonitrile solution of N-methyl-N-(trimethylsilyl)-trifluoroacetamide and a suitable heterocyclic compound of Formula 2, 3 or 4 at ambient temperature to give B-7. The benzyloxycarbonyl group at the C₃ amino group is removed by known methods to give compound B-8 and the free amine is couple with a carboxylic acid in the presence of HOBT and DCC at ambient temperatures. Removal of any remaining protecting groups by known methods gives the N-1-sulfonyl-aminocarbonyl compound, B-5.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1 cis-($\pm$)-4-(Hydroxymethyl)-3-[((phenylmethoxy)-carbonyl)amino]-2-azetidinone

To a stirred solution of zinc chloride (23.2 g) in anhydrous tetrahydrofuran (300 ml) at 0° C. is added sodium borohydride (13.8 g) and the mixture is allowed to warm to room temperature and is stirred overnight. To the mixture is added cis-($\pm$)-4-(methoxycarbonyl)-3-[((phenylmethoxy)carbonyl)amino]-2-azetidinone (39.2 g) and the reaction mixture is slowly heated to 65° C. and stirred at that temperature for 2 hours. The reaction mixture is cooled to 0° C. and 6N hydrochloric acid (200 ml) is added dropwise with stirring. The mixture is poured into ethyl acetate (1 l) and the organic layer is taken. The aqueous layer is saturated with sodium chloride and re-extracted with ethyl acetate (200 ml). The combined organic layer is washed with water (200 ml) and with 200 ml of brine twice and dried over anhydrous sodium sulfate. The solvent is concentrated under reduced pressure to afford a yellow oil which is purified by column chromatography on silica gel (ethyl acetate as eluent) to obtain 24.3 g of the title product. Physical characteristics are as follows:
MP: 98°-100° C.

EXAMPLE 2 cis-($\pm$)-3-[2[(2-t-Butoxycarbonylamino-4-thiazolyl]2-[(1-t-butoxycarbonylmethoxy)imino]]acetamido-4-hydroxymethyl-2-azetidinone To a stirred solution of cis-($\pm$)-4-(Hydroxymethyl)-3-[((phenylmethoxy)-carbonyl)amino]-2-azetidinone (19.5 g) in methanol (150 ml) is added palladium black (7.6 g) slurried in ethanol (25 ml) and the reaction mixture is stirred under one atmosphere of hydrogen gas for 24 hours. Toluene (100 ml) is added to the reaction mixture and it is stirred for 15 minutes. The solid material is filtered and the filtrate solution is concentrated under reduced pressure. The residue is dissolved in methylene dichloride (200 ml) and dimethylformamide (500 ml) and cooled in the ice bath. To this cooled solution, 2-[(2-t-butoxycarbonylamino)-4-thiazolyl]-[(1-t-butoxycarbonylmethoxy)imino]-carboxylic acid (23.8 g) is added followed by dicyclohexylcarbodiimide (12.6 g) and 1-hydroxybenzotriazole (4.2 g). The reaction mixture is stirred for 3 hours at 0° C. The precipitated solid is filtered and the filtrate solution is partitioned between ethyl acetate (2.5 l) and water (1 l). The organic layer is taken and the aqueous layer is washed with 500 ml of ethyl acetate twice. The combined organic layer is washed with aqueous sodium bicarbonate followed by brine and dried over anhydrous sodium sulfate. It is filtered and the filtrate solution is concentrated under reduced pressure and the residual material is chromatographed on silica gel eluting with 1:1 hexane:ethyl acetate and ethyl acetate to obtain 14.1 g of the title compound. Physical characteristics are as follows:
MP: 195° C. (decomp.).

EXAMPLE 3 cis-($\pm$)-3-[2[(2-t-Butoxycarbonylamino-4-thiazolyl]2-[(1-t-butoxycarbonylmethoxy)imino]]acetamido-4-N-formyl-glycinoyloxymethyl-2-azetidinone To a mixture of cis-($\pm$)-3-[2[(2-t-Butoxycarbonylamino-4-thiazolyl]2-[(1 t-butoxycarbonylmethoxy)imino]]acetamido-4-hydroxymethyl-2-azetidinone (4.5 g), 1-hydroxybenzotriazole (1.216 g), dimethylaminopyridine (122 mg), N-formylglycine (1.62 g) and in the presence of a small amount of 4A molecular sieves in 60 ml of methylene dichloride and 6 ml of dimethylformamide, dicyclohexylcarbodiimide (3.25 g) is added with stirring at room temperature. The reaction is complete in 2 hours. The precipitated solid is filtered off, washed with methylene dichloride (50 ml) and the filtrate solution is stirred with aqueous sodium bicarbonate (1.89 g sodium bicarbonate in 40 ml water) at room temperature for 15 minutes. The organic layer is taken, dried over sodium sulfate and concentrated under reduced pressure. The residue is passed through the medium pressure silica gel column eluting with 3:1 hexane:ethyl acetate and ethyl acetate to obtain 3.6 g of the title compound. Physical characteristics are as follows:
MP: 108°-110° C.

EXAMPLE 4

Alternative preparation of cis-($\pm$)-4-(Hydroxy-methyl)-3-[((phenylmethoxy)carbonyl)amino]-2-azetidinone A solution of 1.63 g of sodium borohydride in 25 ml of water is added dropwise to a well stirred solution of 3.0 g of cis-($\pm$)-4-(methoxycarbonyl)-3-[((phenylmethoxy)carbonyl)amino]-2-azetidinone in 190 ml of tetrahydrofuran. The addition is made over a period of 10 minutes while stirring in an ice bath. The reaction is stirred for 3 hours. Methylene dichloride (250 ml) is added followed by anhydrous sodium sulfate. A clear solution is obtained by filtration. The solvent is removed and the residue is dissolved in acetone. The solution is clarified by filtration and concentrated to give 2.84 g of the title compound. Physical characteristics are as follows: $^{13}$C NMR ($\delta$, CH₃OH-d₆): 55.9, 60.2, 61.6 67.9, 128.7–129.3, 137.6, 158, 170.7.

EXAMPLE 5 cis-($\pm$)-4-[Methoxycarbonyl)oxymethyl]-3-[((phenylmethoxy)-carbonyl)amino]-2-azetidinone Methyl chloroformate (2.42 g) is added dropwise to a solution of 3.2 g of cis-($\pm$)-4-(Hydroxy-methyl)-3-[((phenylmethoxy)carbonyl)-amino]-2-azetidinone and 3.03 g of pyridine in 100 ml of methylene dichloride while stirring at 0° C. After one hour an additional 0.5 g of methyl chloroformate is added. The reaction mixture is stirred an additional 0.5 hour and then washed successively with dilute mineral acid (e.g. HCl H₂SO₄), water and potassium bicarbonate solution. Evaporation of the solvent and trituration of the residue with ethyl acetate affords 2.48 g of the title compound. Physical characteristics are as follows: MP: 155°-158° C.

According to the procedures of Example 5, the following compounds are also prepared:

cis-(±)-4-[(Formylaminoethoxycarbonyl)oxymethyl]-3-[((phenylmethoxy)carbonyl)amino]-2-azetidinone;

cis-(±)-4-[(t-Butoxycarbonylaminoethoxycarbonyl)oxymethyl]-3-[((phenylmethoxy)carbonyl)amino]-2-azetidinone;

cis-(±)-4-[(Aminocarbonyloxyethoxycarbonyl)oxymethyl]-3-[((phenylmethoxy)carbonyl)amino]-2-azetidinone; and cis-(±)-4-[(Chloroethoxycarbonyl)oxymethyl]-3-[((phenylmethoxy)-carbonyl)amino]-2-azetidinone.

EXAMPLE 6 cis-(±)-1-[(Chlorosulfonyl)aminocarbonyl]-4-[(methoxycarbonyl)oxymethyl]-3-[((phenylmethoxy)carbonyl)-amino]-2-azetidinone Chlorosulfonyl isocyanate (175 mg) is added dropwise to a suspension of 382 mg of cis-(±)-4-[Methoxycarbonyl)oxymethyl]-3-[((phenylmethoxy)-carbonyl)amino]-2-azetidinone in 8 ml of methylene dichloride while stirring in an ice bath. The bath is removed after 20 minutes and the mixture stirred at ambient conditions. Evaporation of the solvent under vacuum leaves the title compound as a glass which is used without purification.

According to the procedure of Example 6, the following chlorosulfonyl compounds are also prepared:

cis-(±)-1-[(Chlorosulfonyl)aminocarbonyl]-4-[(formylaminoethoxycarbonyl)-oxymethyl]-3-[((phenylmethoxy)carbonyl)amino]-2-azetidinone;

cis -(±)-1-[(Chlorosulfonyl)aminocarbonyl]-4-[(t-butoxycarbonylaminoethoxycarbonyl)-oxymethyl]-3-[((phenylmethoxy)carbonyl)amino]-2-azetidinone;

cis-(±)-1-[(Chlorosulfonyl)aminocarbonyl]-4-[(aminocarbonyloxyethoxycarbonyl)-oxymethyl]-3-[((phenylmethoxy)carbonyl)amino]-2-azetidinone; and cis-(±)-1-[(Chlorosulfonyl)aminocarbonyl]-4-[(chloroethoxycarbonyl)oxymethyl]-3-[((phenylmethoxy)carbonyl)amino]-2-azetidinone.

EXAMPLE 7

N-2,5-Dioxoimidazolidinyl-1,4-dihydro-4-oxo-5-(phenylmethoxy)-2-pyridine carboxamide To a mixture of 3-aminohydantoin (2.35 g), pyridone carboxylic acid (5.0 g), pyridine hydrochloride (3.63 g) and hydroxybenzotriazole (1.34 g) in pyridine (80 ml) under an atmosphere of argon is added a solution of dicyclohexylcarbodiimide (7.57 g) in pyridine (10 ml). The mixture is heated at 50° C. for 2 days. Residual solids are removed by filtration through celite washing with pyridine. Pyridine is removed from the filtrate by bulb-to-bulb distillation under vacuum. The reside is purified by silica gel chromatography (67 cm×5 cm silica gel 60 (63–200 μm) column eluted with the following gradient of methanol/methylene chloride: 2 L of 2%, 2.5 L of 5% and 1 L each of 7%, 10%, 15%, 20%, 25% and 30%. The following fractions are collected: 1–4, 0.500 ml each; 5–17, 250 ml each; 18–40, 125 ml each, and 41–49, 250 ml each. Fractions 42–46 are combined and concentrated to give 2.77 g of the title compound. Physical characteristics are as follows:

TLC (10% methanol/methylene chloride, UV): Rf=0.33.

EXAMPLE 8

N-2,5-Dioxoimidazolidinyl-1,4-dihydro-4-oxo-5-hydroxy-2-pyridine carboxamide

A mixture of N-2,5-dioxoimidazolidinyl-1,4-dihydro-4-oxo-5-(phenylmethoxy)-2-pyridine carboxamide (303 mg) and 10% palladium on carbon (115 mg) in DMF (4 ml) is evacuated and placed under an atmosphere of H$_2$. After 2 hours the mixture is filtered through celite and the filtrate is concentrated to give 292 mg of the title compound. Physical characteristics are as follows:

$^1$H NMR (DMSO-d$_6$): δ 8.06, 7.5, 4.1.
$^1$H NMR (CD$_3$OD): δ 7.5, 4.29, 1.46.

EXAMPLE 9

2-[[[1-[2-[[(1,1-Dimethylethoxy)carbonyl]amino]-4-thiazolyl]-2-[[1-[[[[3-[[(1,4-dihydro-4-oxo-5-hydroxy-2-pyridinyl)carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 1,1-dimethylethyl ester A solution of N-methyl-N-(trimethylsilyl)trifluoroacetamide (140 μl) and N-2,5-dioxoimidazolidinyl-1,4-dihydro-4-oxo-5-hydroxy-2-pyridine carboxamide (50 mg) in acetonitrile (0.7 ml) is cooled to about 0° C. and added to a suspension of chlorosulfonylisocyanate and 2-[[[1-[2-[[(1,1-dimethylethoxy)carbonyl]amino]-4-thiazolyl]-2-oxo-2-[(2-oxo-3-azetidinyl)amino]ethylidene]amino]oxy]-2-methyl propanoic acid 1,1-dimethyl ester under an argon atmosphere. The mixture is warmed to room temperature over 16 hours, partitioned between ethyl acetate (3 ml) and water (3 ml). The aqueous layer is extracted twice with ethyl acetate (3 ml). The combined organic layers are combined and concentrated to give 139 mg of the title compound. Physical characteristics are as follow:

HPLC (60% acetonitrile/40% 0.005M tetra-n-butylammonium: sulfate, pH3) Rt 5.48 minutes.

EXAMPLE 10

2-[[[1 (2-Amino-4-thiazolyl)-2-[[1-[[[[3-[[(1,4-dihydro-4-oxo-5-hydroxy-2-pyridinyl)carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 1,1-dimethylethyl ester potassium salt 2-[[[1-[2-[[(1,1-Dimethylethoxy)carbonyl]amino]-4 thiazolyl]-2-[[1-[[[[3-[[(1,4-dihydro-4-oxo-5-hydroxy-2-pyridinyl)carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 1,1-dimethylethyl ester (128 mg) is cooled to 0° C. and dissolved in cold trifluoroacetic acid (4 ml). After 30 minutes, the solution is warmed to room temperature and concentrated. The residue is dissolved in water (10 ml) by adjusting to pH7 with 0.5M aqueous potassium bicarbonate and lyophilized to give the title compound.

EXAMPLE 11

2-[[[1-(2-Amino-4-thiazolyl)-2-[[1-[[[3 [[(1,4-dihydro-4-oxo-5-hydroxy-2-pyridinyl)carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 2-[[[1-[2 [[(1,1-Dimethylethoxy)carbonyl]amino]-4-thiazolyl]-2-[[1-[[[3-[[(1,4-dihydro-4-oxo-5-hydroxy-2-pyridinyl)carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 1,1-dimethylethyl ester (833 mg) is cooled to 0° C. and dissolved in cold trifluoroacetic acid (20 ml). After 45 minutes, the solution is warmed to room temperature, stirred for 2 hours and concentrated. The residue is dissolved in 1:1::acetonitrile:water (6 ml) and chromatographed over HP-20 to give the title compound. Physical characteristics are as follows:

Mass spectrum (FAB): m/e 699, 385.

EXAMPLE 12

Piperazine, 1-[[1,4-dihydro-4-oxo-5-(phenylmethoxy)-2-pyridinyl]carbonyl]-4-(2,2-dimethyl-1-oxopropyl)

To a suspension of 5-benzyloxy-2-pyrid-4-one-carboxylic acid (2.63 g) in dry DMF (80 ml) is added N-t-butoxycarbonyl piperazine (2.0 g), dicyclohexylcarbodiimide (2.22 g), N-hydroxybenzotriazole (1.45 g) and 4-dimethylaminopyridine (50 mg). The mixture is stirred 5 hours at room temperature under a nitrogen atmosphere and then stored 16 hours in the refrigerator. The mixture is filtered and concentrated to dryness. The residue is dissolved in chloroform (250 ml) and extracted with 5% aqueous sodium bicarbonate (2×100 ml), brine (100 ml) and dried over sodium sulfate. The solvent is removed and the crude product is chromatographed on 250 g of silica gel eluting with 2% methanol/methylene chloride (500 ml), 4% methanol/methylene chloride (500 ml), 6% methanol/methylene chloride (1 l) and 10% methanol/methylene chloride (1l). The chromatographed product is recrystallized in 25% methanol/methylene chloride and ethyl acetate to give 3.21 g of the title compound. Physical characteristics are as follows:

M.P. 191°–194°.

EXAMPLE 13

Piperazine, 1-[[1,4-bis(phenylmethoxy)-2-pyridinyl]-carbonyl]-4-(2,2-dimethyl-1-oxopropyl)-

To a suspension of piperazine, 1-[[1,4-dihydro-4-oxo-5-(phenylmethoxy)-2-pyridinyl]carbonyl]-4-(2,2-dimethyl-1-oxopropyl)-(500 mg) in dry DMF (5 ml) is added benzyl bromide (155 μl) and triethylamine (250 μl). The mixture is stirred under nitrogen at room temperature. Additional benzyl bromide (155 μl) and triethylamine (250 μl) are added and the mixture stirred for 24 hours. The solvent is removed and the residue partitioned between methylene chloride (40 ml) and water (5 ml). The organic layer is dried and concentrated to give 700 mg crude product which is dissolved in ethyl acetate and filtered. The residue is purified by thick layer chromatography on three silica gel plates eluted with 3% methanol/ethyl acetate. The desired product is collected and washed from the support with 10% methanol/chloroform to give 179 mg of the title compound. Physical characteristics are as follows:

IR 2975, 2927, 1695, 1646 1581, 1230, 1167 cm$^{-1}$.

EXAMPLE 14

Piperazine, 1-[[1,4-bis(phenylmethoxy)-2-pyridinyl]carbonyl]-4-(2,2-dimethyl-1-oxopropyl)-

To a solution of piperazine, 1-[[4,5-bis(phenylmethoxy)-2-pyridinyl]carbonyl]-4-(2,2-dimethyl-1-oxopropyl)- (110 mg) in methylene chloride (3 ml) is added trifluoroacetic acid (1 ml). The mixture is stirred 10 minutes at room temperature and concentrated. The residue is triturated with diethyl ether and partitioned between methylene chloride (10 ml) and water (5 ml). The aqueous layer is adjusted to pH8 with saturated sodium carbonate and separated. The organic layer is dried over sodium sulfate and concentrated to give 82 mg of the title compound. Physical characteristics are as follows:

$^1$H NMR (CDCl$_3$) δ 7.3, 7.07, 6.9, 6.28, 4.5–5.3, 2.0–3.8

EXAMPLE 15

Piperazinone, 4-[[1,4-bis(phenylmethoxy)-2-pyridinyl]-carbonyl]

To a solution of 2-oxopiperazine (48 mg) and 4,5-dibenzyloxy-2-pyridine carboxylic acid (150 mg) in dry DMF (3 ml) is added dicyclohexylcarbodiimide (99 mg) and N-hydroxy benzotriazole (65 mg). The mixture is stirred 16 hours at room temperature, filtered and concentrated. The residue is partitioned between methylene chloride (50 ml) and 5% aqueous sodium bicarbonate (20 ml). The organic layer is washed with brine, dried over sodium sulfate and concentrated to give 26 mg crude product. The crude product is chromatographed on 10 g silica gel packed with methylene chloride and eluted with 50 ml each of 3%, 6% 10% and 15% methanol/chloroform to give 140 mg of the title compound. Physical characteristics are as follows:

IR 3200, 1672, 1651, 1615, 1577 1228 cm$^{-1}$.

EXAMPLE 16

1,2,4-Triazin-3(2H)-one, 1-[[1,4-dihydro-4-oxo-5-(phenylmethoxy)-2-pyridinyl]-carbonyl]tetrahydro To a solution of tetrahydro-1,2,4-triazin-3(2H)-one (10 g) and 5-benzyloxy-2-pyrid-4-one carboxylic acid (2.4 g) in dry DMF (50 ml) is added 1-hydroxybenzotriazole (0.66 g) and 1,3-diisopropylcarbodiimide (1.55 ml). After stirring 24 hours at room temperature, additional 1,3-diisopropylcarbodiimide (0.77 ml) is added over 40 hours. The mixture is filtered, the DMF is removed and the residue is dissolved in chloroform and filtered. The filtrate is chromatographed over 200 ml silica gel and eluted with chloroform (350 ml), 1% methanol/chloroform (400 ml), 3% methanol/chloroform (400 ml), 5% methanol/chloroform (700 ml), 7% methanol/chloroform (800 ml), 10% methanol/chloroform (400 ml) and 15% methanol/chloroform (200 ml). The fractions are concentrated and the resulting residue recrystallized from methanol to give 0.978 g of the title compound. Physical characteristics are as follows:

$^1$H NMR (DMSO-d$_6$) δ 8.1314, 7.25–7.58, 7.18, 7.05, 5.21, 3.05–4.32.

EXAMPLE 17

Propanoic acid,
2-[[[1-(2-amino-4-thiazolyl)-2-[[1-[[[[4-[1,4-dihydro-5-hydroxy-4-oxo-pyridinyl)carbonyl]-2-oxo-3-azetidinyl]amino]-2-oxoethylidene]amino-]oxy]-2-methyl-, [S,(Z)]

To a suspension of piperazinone, 4-[[4,5-bis(phenylmethoxy)-2-pyridinyl]carbonyl]-(200 mg) in dry THF (5 ml) is added N-methyl-N-trimethylsilyltrifluoroacetamide (0.53 ml). The mixture is stirred 1.25 hours at room temperature under nitrogen and then concentrated to dryness. The residue is dissolved in dry THF (5 ml). To a suspension of 3-[2-(2-t-butoxycarbonylamino-4-triazolyl)-2-(t-butoxycarbonylisopropyloxyimino)acetamido]-2-azetidinone (238 mg) in methylene chloride (4 ml), stirred at 0° under nitrogen, is added chlorosulfonylisocyanate (50 µl). The mixture is stirred 40 minutes at 0° and the THF solution of silylated amide is added. The mixture is allowed to warm to room temperature and stirred 3 hours. The solvent is removed and the residue partitioned between methylene chloride (75 ml) and phosphate buffer (pH 6.3, 8 ml). The aqueous phase is extracted with methylene chloride (10 ml) and the combined organic layers are dried over sodium sulfate and concentrated. The residue is dissolved in methanol (15 ml) and palladium black (350 mg) is added. The mixture is stirred 2.75 hours at room temperature under a hydrogen atmosphere. The mixture is filtered and the filtrate is concentrated. The residue is dissolved in methylene chloride (10 ml) and cooled to 0°, under nitrogen. Trifluoroacetic acid (10 ml) is added and the reaction mixture stirred 30 minutes at 0°, 1.5 hours at room temperature, and concentrated. The residue is triturated with diethyl ether and chromatographed on a 200 ml bed of HP-20 resin eluting with water (400 ml), 1, 3, 7 and 9% acetonitrile/water (200 ml each) and 10, 15 and 20% acetonitrile/water taking 40 ml fractions. The fractions are bioassayed using *Pseudomonas aeruginosa*. Fractions 6-11 are combined and lyophilized to give 144 mg of the title compound. Physical characteristics are as follows:

IR 3150, 1782, 1650, 1300, 1145 cm$^{-1}$; MS (FAB) 684.

EXAMPLE 18

Propanoic acid,
2-[[[1-(2-amino-4-thiazolyl)-2-[[1-[[[[1-[(1,4-dihydro-5-hydroxy-4-oxo-2-pyridinyl)carbonyl]tetrahydro-3-oxo-1,2,4-triazin-4(1H)-yl]sulfonyl]amino]carbonyl]-2-oxo-3-azetidinyl]amino]-2-oxoethylidene]amino]oxy]-2-methyl- [S-(Z)]-

To a suspension of 1,2,4-triazin-3(2H)-one, 1-[[1,4-dihydro-4-oxo-5-(phenylmethoxy)-2-pyridinyl]carbonyl]tetrahydro- (130 mg) in THF (3 ml) is added N-methyl-N-trimethylsilyltrifluoroacetamide (0.22 ml) and stirred at room temperature for 2 hours. To 3-[2-(2-t-butoxycarbonylamino-4-thiazol- (200 mg) in methylene chloride is added chlorosulfonylisocyanate (42 µl) at 0° C. The mixture is stirred for 35 minutes at 0° and the THF solution of silylated amide is added. After 2 hours methanol (80 µl) is added, the mixture is stirred for 10 minutes and concentrated. The residue is dissolved in methanol (3 ml) and Pd black (200 mg) is added and the reaction put under a hydrogen atmosphere. After 1.5 hours, the mixture is filtered and concentrated. The residue is dissolved in methylene chloride (2 ml), cooled to 0° C. and trifluoroacetic acid added. After 10 minutes, the ice bath is removed and the mixture is stirred at room temperature for one hour. The solution is concentrated, triturated with diethyl ether and chromatographed over 100 ml HP-20. The column is eluted with 300 ml water, 50 ml—5%, 200 ml—1%, 100 ml—2%, 100 ml—3%, 200 ml—5%, 200 ml—10%, 100 ml—15%, 200 ml—20%, 200 ml—30% and 200 ml—50% acetonitrile/water. The fractions are bioassayed using *Pseudomonas aeruginosa*.

EXAMPLE 19

Acetic acid,
2-[[[1-(2-amino-4-thiazolyl)-2-[[1-[[[[4-[(1,4-dihydro-5-hydroxy-4-oxo-2-pyridinyl)carbonyl]-1-piperazinyl]sulfonyl]amino]carbonyl]-2-oxo-3-azetidinyl]amino]-2-oxoethylidene]amino]oxy]-, [S-(Z)]-

To a 0° C. suspension of 3-[2-(t-butoxycarbonylamino)-4-thiazolyl]-2-t-butoxycarbonylmethoxyimino]acetamido]-2-azetidinone (0.12 g) in methylene chloride (2.5 ml) is added chlorosulfonyl isocyanate (26 µl). After one hour additional chlorosulfonyl isocyanate (4 µl) is added. After 30 minutes, the mixture is added to a 0° C. solution of piperazine, 1-[[4,5-bis(phenylmethoxy)-2-pyridinyl]carbonyl]- (0.10 g) and triethylamine (0.11 ml) in THF (1.6 ml). After 2 hours, the reaction is quenched with methanol (0.4 ml). The solution is concentrated and dried. The residue is dissolved in methanol (7 ml) under N$_2$, Pd black (0.20 g) is added and the mixture put under a hydrogen atmosphere. After one hour, the mixture is filtered and the filtrate is concentrated. The crude solid is dissolved in methylene chloride (3 ml) and trifluoroacetic acid (1.00 ml) is added at 0° C. The reaction is allowed to warm to room temperature. After one hour, the mixture is concentrated and the residue is triturated with diethyl ether. The solid obtained is dried and chromatographed over 125 ml Hp-20 resin. The column is eluted with 200 ml water, 200 ml—1%, 200 ml—2%, 100 ml—3%, 100 ml—4%, 100 ml—6%, 100 ml each of 8%, 10% and 15%, 300 ml—20% and 200 ml—50% acetonitrile/water taking 15 ml fractions which are bioassayed using *Klobsiella pneumoniae* and *Escherichia coli*. Bioactive fractions are pooled and lyophilized to give 0.030 g of the title compound. Physical characteristics are as follows:

MS (FAB) calculated: 642.1037; found: 642.1062.
IR 3150, 1780, 1630 cm$^{-1}$.

EXAMPLE 20

2-Pyridinecarboxylic acid,
1,4-dihydro-4-oxo-5-(phenylmethoxy)-,
2-(aminocarbonyl)hydrazide A mixture of hydrazinecarboxamide (0.732 g), hydroxybenzotriazole (0.886 g), 5-benzyloxy-4-pyridone-2-carboxylic acid (1.609 g) and triethylamine (1.00 ml) in DMF (25 ml) is treated with dicyclohexylcarbodiimide (1.353 g) at room temperature. The mixture is stirred overnight at room temperature, filtered and concentrated. The residue is stirred in water (20 ml) for several hours, diluted with saturated sodium bicarbonate (20 ml) and filtered. The residue is suspended in water (20 ml), the pH is adjusted to 12 with 10% aqueous potassium hydroxide, stirred at room temperature for 30 minutes and filtered. The filtrate is acidified to pH 4-5 with 6N hydrochloric acid, the precipitate is filtered, washed with water and dried to give 1.513 g of the title compound. Physical characteristics are as follows:

M.P. 190°–193° C.

According to the procedure of Example 20, the following compounds are also prepared:

2-pyridinecarboxylic acid, 1,4-dihydro-4-oxo-5-(phenylmethoxy)-, 2-[(methylamino)carbonyl]hydrazide, physical characteristics are:

M.P. 225°–227° C.; and 2-(N-ethylaminocarbonylhydrazinyl)carbonyl-5-benzyloxy-4-pyridone, physical characteristics are:

IR (ATR) 3321, 2933, 1646, 1609, 1544, 1510, 1271 cm$^{-1}$.

EXAMPLE 21

4(1H-Pyridinone, 2-(2,5-dihydro-5-oxo-1H-1,2,4-triazol-3-yl)-5-(phenylmethoxy)-

A solution of 2-pyridinecarboxylic acid, 1,4-dihydro-4-oxo-5-(phenylmethoxy)-, 2-(aminocarbonyl)hydrazide (3.00 g) in 10% aqueous potassium hydroxide is refluxed for one hour. The solution is cooled to 0° C., acidified to pH 7 with concentrated hydrochloric acid, filtered and dried to give 1.026 g of the title compound. Physical characteristics are as follows:

M.S. (FAB) 285.

According to the procedure of Example 21, the following compound is also prepared:

4-(1H)-Pyridinone, 2-(4,5-dihydro-4-methyl-5-oxo-1H,1,2,4-triazol-3-yl)-5-(phenylmethoxy)-,physical characteristics are:

M.P. 204°–205° C.

EXAMPLE 22

Propanoic acid, 2-[[[2-[[1-[[[[3-[1,4-dihydro-4-oxo-5-(phenylmethoxy)-2-pyridinyl]-4,5-dihydro-4-methyl-5-oxo-1H-1,2,-4-triazol-1-yl]sulfonyl]-amino]carbonyl]-2-oxo-3-azetidinyl]amino]-1-[2-[[(1,1-dimethylethoxy)carbonyl]amino]-4-thiazolyl)-2-oxoethylidene]amino]oxy]-2-methyl-, 1,1-dimethylethyl ester, [S-(Z)]-

A solution of N-methyl-N-(trimethylsilyl)trifluoroacetamide (1.341 ml) and 4(1H)-pyridinone, 2-(2,5-dihydro-5-oxo-1H-1,2,4-triazolyl-3-yl)-5-(phenylmethoxy)- (360 mg) in THF (10 ml) is stirred at room temperature for 45 minutes, concentrated, taken up in THF (10 ml) and added immediately to a solution prepared by adding chlorosulfonylisocyanate (0.126 ml) to a solution cooled to about 0° C. of propanoic acid, 2-[[[1-[2-[[(1,1-dimethylethoxy)carbonyl]amino]-4-thiazolyl]-2-oxo-2-[(2-oxo-3-azetidinyl)amino]ethylidene]amino]oxy]-2-methyl-, 1,1-dimethylethyl ester, (S)- (600 mg) in methylene chloride (10 ml). After one hour the mixture is concentrated, partitioned between ethyl acetate and water, the aqueous layer is extracted with ethyl acetate, the combined organic layers are dried over sodium sulfate, filtered and concentrated to give 1.113 g of the title compound. Physical characteristics are as follows:

HPLC (70% acetonitrile/40% 0.05M tetra-n-butylammonium sulfate, flow rate 1.25 ml/min) R$_t$ 4.19 minutes.

According to the procedure of Example 22, the following compound is also prepared:

propanoic acid, 2-[[[2-[[1-[[[[3-[1,4-dihydro-4-oxo-5-(phenylmethoxy)-2-pyridinyl]2,5-dihydro-5-oxo--1H-1,2,4-triazol-1-yl]sulfonyl]amino]carbonyl]-2-oxo-3-azetidinyl]amino]-1-[2-[[1,1-dimethylethoxy)carbonyl]amino]-4-thiazolyl]-2-oxoethylidene]amino]oxy]-2-methyl-, 1,1-dimethylethyl ester, [S-(Z)]-, physical characteristics are:

HPLC (60% acetonitrile/40% 0.05M tetra-n-butylammonium sulfate, flow rate 1.25 ml/min) R$_t$ 7.75 minutes.

EXAMPLE 23

Propanoic acid, 2-[[[1-(2-amino-4-thiazolyl)-2-[[1-[[[[3-(1,4-dihydro-5-hydroxy-4-oxo-2-pyridinyl)-4,5-dihydro-4-methyl-5-oxo-1H-1,2,4-triazol-1-yl]sulfonyl]amino]carbonyl-2-oxo-3-azetidinyl]amino-2-oxoethylidene)amino]oxy]-2-methyl-, [S-(Z)]-

Palladium black (1.0 g) is added to a solution of propanoic acid, 2-[[[2-[[1-[[[[3-[1,4-dihydro-4-oxo-5-(phenylmethoxy)-2-pyridinyl]-4,5-dihydro-4-methyl-5-oxo-1H-1,2,4-triazol-1-yl]sulfonyl]amino]carbonyl]-2-oxo-3-azetidinyl]amino]-1-[2-[[(1,1-dimethylethoxy)carbonyl]-amino]-4-thiazolyl]-2-oxoethylidene]amino]oxy-2-methyl-, 1,1-dimethyl ethyl ester, [S-(Z)]- in methanol and stirred under a hydrogen atmosphere for 45 minutes. The mixture is filtered and the crude product is purified by column chromatography. The debenzylated product (289 mg) is dissolved in methylene chloride (10 ml), cooled to 0° C. and treated with trifluoroacetic acid (10 ml). After addition the mixture is stirred at room temperature for 2 hours and concentrated. The residue is purified by column chromatography to give 59.4 mg of the title compound. Physical characteristics are as follows:

M.S. (FAB) 655.

According to the procedure of Example 23, the following compound is also prepared:

propanoic acid, 2-[[[1-(2-amino-4-thiazolyl)-2-[[1-[[[[3-(1,4-dihydro-5-hydroxy-4-oxo-2-pyridinyl)-2,5-dihydro-5-oxo-1H-1,2,4-triazol-1-yl]sulfonyl]amino]-carbonyl]-2-oxo-3-azetidinyl]amino]-2-oxoethylidene]amino]oxy]-2-methyl-, [S-(Z)]-, physical characteristics are:

M.S. (FAB) 641.0832.

EXAMPLE 24

5-Aminomethyl-2-oxazolidinone

A solution of 5-chloromethyl-2-oxazolidinone (1.7 g) and sodium azide (1.5 g) in DMF (10 ml) is stirred at 95° C. for 3 days then poured into water (50 ml) and extracted with methylene chloride (5×25 ml) and ethyl acetate (2×25 ml). The combined extracts are dried over magnesium sulfate, filtered, and concentrated. The residue is diluted with ethyl acetate (4 ml) and ethanol (25 ml), 10% palladium on carbon is added and the mixture is subjected to 40 psi of hydrogen for 27 hours. The mixture is filtered and the solvent is removed to give 0.510 g of the title compound. Physical characteristics are as follows:

TLC (4:1 chloroform/methanol, p-anisaldehyde stain): R$_f$=0.14.

EXAMPLE 25

N-[(2-Oxo-5-oxazolidinyl)methyl]-1,4-dihydro-4-oxo-5-(phenylmethoxy)-α-pyridinecarboxamide A mixture of 5-aminomethyl-2-oxazolidinone (3.37 g), 1,3-dicyclohexylcarbodiimide (6.19 g), 1-hydroxybenzotriazole (4.05 g), 1,4-dihydro-4-oxo-5-(phenylmethoxy)-α-pyridinecarboxamide (7.35 g), and N,N- dimethylaminopyridine (0.367 g) in DMF (70 ml) is stirred for 2½ days at room temperature. The mixture is filtered and concentrated. The residue is purified by MPLC (5.5×31 cm, 40–63μ silica gel column, eluted with 10% methanol/chloroform) to give 5.45 g of the title compound. Physical characteristics are as follows:

TLC (4:1 chloroform/methanol); $R_f$=0.45.

EXAMPLE 26

N-[(2-Oxo-5-oxazolidinyl)methyl]-1,4-dihydro-5-hydroxy-4-oxo-2-pyridine carboxamide Palladium black (0.72 g) is added to a solution of N-[(2-oxo-4-oxazolidinyl)methyl]-1,4-dihydro-4-oxo-5-(phenylmethoxy)-α-pyridinecarboxamide (2.79 g) in DMF (45 ml). The mixture is stirred under hydrogen for 3 hours. The mixture is filtered and the DMF removed to give 1.99 g of the title compound. Physical characteristics are as follows:

TLC (4:1 chloroform/methanol); $R_f$=0–0.25.

EXAMPLE 27

[[[1-(α[[-1-[[[[4-[[(1,4-dihydro-5-hydroxy-4-oxo-2-pyridinyl)carbonyl]amino]-[2-oxo-4-oxazolidinyl]methyl]-sulfonyl]amino]carbonyl]-2-oxo-3-azetidinyl]amino]-2-[2-[[1,1-dimethylethoxy)carbonyl]amino]-4-thiazolyl]-2-oxoethylidene]amino]oxy]acetic acid 1,1-dimethylethyl ester In a 10 ml flame-dried round-bottom flask, N-[(2-oxo-5-oxozolidinyl)methyl]-1,4-dihydro-5-hydroxy-4-oxo-2-pyridine carboxamide (61 mg) is suspended in 4:1::methylene chloride:acetonitrile (1.25 ml) and bis(-trimethylsilyl)trifluoroacetamide (1.27 ml) is added. After 2.5 hours the solvents are evaporated and the mixture is placed under high vacuum to give a cloudy oil.

In a separate flame-dried 10 ml flask, [[[2-[[1-[[[chlorosulfonyl]amino]carbonyl]-2-oxo-3-azetidinyl]amino]-1-[2-[[1,1-dimethylethoxy]carbonyl]amino]-4-thiazolyl]-2-oxoethylidene]amino]oxy]acetic acid 1,1-dimethylethyl ester (112 mg) is suspended in 4:1::methylene chloride:acetonitrile and cooled to −15° C. in an ice-methanol bath and chlorosulformyl isocyanate (21 μl and 4.2 μl)) is added in two portions. After one hour this mixture solution is added to the silylated mixture at 0° C. The mixture is stirred for 2 hours at 0° C., 16 hours at 25° C., then partitioned between 0.5M aqueous potassium bicarbonate (25 ml) and ethyl acetate (20 ml). The aqueous layer is acidified to pH 2 and extracted 6 times with ethyl acetate. The combined extracts are concentrated, dried over magnesium sulfate, filtered, and concentrated to give the title compound. Physical characteristics are as follows:

HPLC (60% CH₃CN/0.05M nBu₄NHSO₄, 1.25 ml/min) $R_t$=3.17 minutes.

The title compound is taken up in trifluoroacetic acid (10 ml) at 0° C. and the solution warmed to ambient temperature over 0.5 hours. The trifluoroacetic acid is removed in vacuo, methylene chloride is added, and then removed in vacuo (twice) to remove residual acid. The residue is taken up in water (30 ml) and the pH adjusted to 7 with solid potassium bicarbonate. Lyophilization gives 100 mg of [[[1-(2-amino-4-thiazolyl)-2-[[1-[[[[4-[[(1,4-dihydro-5-hydroxy-4-oxo-2-pyridinyl)-carbonyl]amino]-[2-oxo-5-oxazolydinyl]methyl]sulfonyl]amino]carbonyl]-2-oxo-3-azetidinyl]amino]-2-oxoethylidene]amino]oxy] acetic acid. Physical characteristics are as follows:

HPLC (35% CH₃CN/0.005M n-Bu₄NHSO₄, pH 3, 1.3 ml/min, Beckman Ultrasphere ODS 5μ, 25 cm×4.6 mm) $R_t$=2.10.

Following similar procedures described in Example 27 the following compounds are also prepared:

2-[[[2-[[1-[[[[4-[[(1,4-dihydro-5-hydroxy-4-oxo-2-pyridinyl)carbonyl]amino]-[2-oxo-5-oxazolidinyl]methyl]-sulfonyl]amino]carbonyl]-2-oxo-3-acetidinyl]amino-1-[2-[[(1,1-dimethylethoxy)carbonyl]amino]-4-thiazolyl]-2-oxoethylidene]amino]oxy]-2-methyl propanoic acid 1,1-dimethylethyl ester. Physical characteristics are as follows:

HPLC (35% CH₃CN/0.005M n-Bu₄NHSO₄, pH 3.0, 1.3 ml/min) Rt=5.57.

2-[[[1-(2-amino-4-thiazolyl)-2-[[1-[[[[4-[[(1,4-dihydro-5-hydroxy-4-oxo-2-pyridinyl)carbonyl]amino]-[2-oxo-5-oxazolidinyl]methyl]sulfonyl]amino]carbonyl]-2-oxo-3-azetidinyl]amino]-2-oxoethylidene]amino]oxy]-2-methyl propanoic acid. Physical characteristics are as follows:

HPLC (35% CH₃CN/0.005M n-Bu₄NHSO₄, pH 3.0, 1.3 ml/min) Rt=3.47.

EXAMPLE 28

Compound E28(b)

To a stirred suspension of compound E28(a) (8.13 g, 0.033 moles) in chloroform (20 ml) and diethyl ether (20 ml) is added an ethereal solution of phenyldiazomethane (25 ml, ca. 1.5 equivalents). The reaction mixture is stirred at room temperature under nitrogen. After 1.5 hours and 4 hours two additional 50 ml aliquots of chloroform is added to solubilize the starting material, and after 4.5 hours another 9 ml of phenyldiazomethane solution is added. After 24 hours, the reaction mixture is evaporated to dryness and the residue chromatographed to give compound E28(b) (7.46 g). Physical characteristics are as follows:

MS (EI): Calc. for $C_{20}H_{10}O_5$: 336.0998, obs.: 336.1005.

EXAMPLE 29

Compound E29

To a stirred solution of compound E28(b) (7.45 g, 0.022 moles) in methanol (300 ml), cooled to 0° C., is added sodium hydroxide (1.0 g, 0.025 moles). After 30 minutes at 0° C., the reaction mixture is neutralized with 6N hydrochloric acid and the methanol is removed in vacuo. The residue is partitioned between chloroform and water and the organic layer removed. The aqueous layer is further extracted with chloroform (2×150 ml), the combined layers dried over sodium sulfate, and the solvent is removed. The residue is chromatographed to give compound E29 (5.22 g). Physical characteristics are as follows:

MS(EI): Calc. for $C_{13}H_{12}O_4$: 232.0735, obs, 232.0742.

EXAMPLE 30

Compound E30

To a stirred solution of compound E29 (978 mg, 4.2 mmoles) in acetone (50 ml), cooled to −5° C., is added dropwise Jones Reagent (8N, 7 ml, 13 eq.). After 3 hours at −5° to 0° C., the reaction mixture is quenched with methanol and filtered. The filtrate is evaporated, diluted with cold water, and filtered. The residue is washed with water and dried to give compound E30

(400 mg). Physical characteristics are as follows: m.p. 144°–145° C.

EXAMPLE 31

Compound E31

To a stirred solution of compound E30 (1.22 g, 0.0050 moles) in DMF (15 ml), heated to 60° C., is slowly added concentrated ammonium hydroxide (58%, 30 ml). The reaction mixture is heated at 50°–60° C. for 2.5 hours. The solvent is removed and the residue is dissolved in DMF, filtered, and evaporated to give crude product which is taken up and evaporated from methanol several times to give compound E31 (1.38 g).

EXAMPLE 32

Compound E32, 2-Pyridinecarboxylic acid, 1-cyclopropyl-1,4-dihydro-4-oxo-5-(phenylmethoxy)-

A solution of compound E33(a) (3.0 g, 0.012 moles), cyclopropylamine (20 ml), and water (2 ml) is heated to reflux temperature for 4.5 hours. The reaction mixture is cooled and evaporated to dryness. The residue is chromatographed to give crude product which is dissolved in water (50 ml), cooled to 0° C., and acidified to pH 2 with 6N hydrochloric acid. The precipitated solid is filtered and dried to give E32 (1.66 g). Physical characteristics are as follows: m.p. 179°–180° C. (dec.).

IR (nujol): 1651, 1576, 1539, 1293, 998, and 751 cm$^{-1}$.

EXAMPLE 33

Compound E33, 2-Pyridinecarboxylic acid, 1,4-dihydro-1-methyl-4-oxo-5-(phenylmethoxy)-

Aqueous methylamine (40%) in water (150 ml) is added to compound E33(a) (12.31 g) and the solution is stirred at 40° C. for 3 hours. The solution is allowed to cool and stirred overnight at room temperature. The excess methylamine is removed in vacuo. The residue is dissolved in water (50 ml) and acidified with 10% hydrochloric acid (about 15 ml). The product is filtered and dried to give compound E33 (11.8 g). Physical characteristics are as follows:

$^{13}$C-NMR (CD$_3$OD) δ 43.2, 72.3, 114.6, 128.5, 129.1, 129.4, 129.5, 137.6, 149, 150.0, 168, 173.

MS (FAB) (M+H)$^+$ calc. for C$_{14}$H$_{14}$N$_1$O$_4$: 260.0923; meas: 260.0917.

EXAMPLE 34

Compound E34, 2-Pyridinecarboxylic acid, 1-butyl-1,4-dihydro-4-oxo-5-(phenylmethoxy)-

Compound E33(a) (2.0 g) is dissolved in n-butylamine (20 ml) and the solution is warmed to 45° C. After 2 hours at 45° C., the mixture is concentrated and the residue is chromatographed. The crude product is dissolved in 1:1 water:methanol (20 ml) and acidified to pH2 with 10% hydrochloric acid. Removal of the methanol gives a solid which is filtered and dried to give compound E34 (1.017 g). Physical characteristics are as follows:

MS (FAB) (M+H)$^+$ calc. for C$_{17}$H$_{20}$N$_1$O$_4$: 302.1392; meas.: 302.1393.

EXAMPLE 35

Compound E35

To a stirred solution of compound E35(a) (6.48 g) in trifluoroacetic acid (85 ml) is added 30% hydrogen peroxide (15 ml). The reaction mixture is heated to 80° C. overnight under a nitrogen atmosphere. The mixture is concentrated to about 15 ml under vacuum and poured into water (600 ml). After cooling, the mixture is filtered and the filtrate is concentrated to give compound 35 (4.45 g). Physical characteristics are as follows:

MS (EI): calc. for C$_6$H$_4$BrNO$_3$: 216.9374; obs.: 216.9366.

EXAMPLE 36

Compound E36, 4-Pyridinecarboxylic acid, 1,2-dihydro-1-hydroxy-2-oxo-

A stirred solution of compound E35 (2.66 g) in 10% aqueous potassium hydroxide solution (50 ml) is heated to 80° C. for 16 hours, cooled to 0° C. and acidified with concentrated hydrochloric acid (25 ml). The solution is cooled, filtered, and washed with water. The solid is dried to give compound E36. Physical characteristics are as follows:

MS (EI): calc. for C$_6$H$_5$NO$_4$: 155.0218; obs.: 155.0214.

EXAMPLE 37

Compound E37

To a stirred solution, under nitrogen, of compound E31 (1.38 g) in DMF (40 ml) is added N-amino-2-imidazolidone (506 mg), dicyclohexylcarbodiimide (1.03 g), hydroxybenzotriazole (676 mg), and N,N-dimethylaminopyridine (61 mg). After 2 hours at room temperature, the mixture is filtered and the filtrate evaporated to dryness. The residue is chromatographed to give compound E37 (577 mg). Physical characteristics are as follows:

$^{13}$C-NMR (MeOD$_4$): 176, 167, 163, 161.89, 148.25, 138.00, 137.05, 130.76, 129.78, 129.53, 118.68, 75.24, 48.08, and 38.01 ppm.

MS (FAB): calc. for C$_{16}$H$_{17}$N$_4$O$_4$: 329.1250; obs: 329.1240.

According to the procedure of Example 37, the following compounds are also prepared:

Compound E37(a), 2-Pyridinecarboxamide, 1-cyclopropyl-1,4-dihydro-4-oxo-N-(2-oxo-1-imidazolidinyl)-5-(phenylmethoxy)-, Physical characteristics are as follows:

MS (EI): calc. for C$_{19}$H$_{20}$N$_4$O$_4$: 368.1484; obs.: 368.1478.

Compound E37(b), 2-Pyridinecarboxamide, 1,6-dihydro-1-hydroxy-6-oxo-N-(2-oxo-1-imidazolidinyl).

Physical characteristics are as follows:

MS (FAB) (M+H)$^+$ calc. for C$_9$H$_{11}$N$_4$O$_4$: 239.0780; obs.: 239.0762.

EXAMPLE 38

Compound E38, 2-Pyridinecarboxamide, 1,4-dihydro-1-methyl-4-oxo-N-(2-oxo-1-imidazolidinyl)-5-(phenylmethoxy)-

Compound E33 (1.0 g) is slurried in DMF (20 ml) in a flame-dried flask under nitrogen and N-amino-2-imidazolidone (0.39 g), diisopropyl carbodiimide (0.6 ml) and 1-hydroxybenzotriazole (0.52 g) added to the suspension. After 2.5 hours, the mixture is filtered and the residue is triturated three times with diethyl ether to remove DMF and dried in vacuo to give E38 (0.564 g). Physical characteristics are as follows:

MS (EI) calc. for C$_{17}$H$_{18}$N$_4$O$_4$: 342.1328; meas.: 342.1322.

According to the procedure of Example 38, the following compounds are also prepared:

Compound E38(a), 2-Pyridinecarboxamide, 1-butyl-1,4-dihydro-4-oxo-N-(2-oxo-1-imidazolidinyl)-5-(phenylmethoxy)-

Physical characteristics are as follows:

MS (FAB) (M·+H)+ calc. for $C_{20}H_{25}N_4O_4$: 385.1876; meas.: 385.1876.

Compound E38(b), 4-Pyridinecarboxamide, 1,2-dihydro-1-hydroxy-2-oxo-N-(2-oxo-1-imidazolidinyl)-.

Physical characteristics are as follows:

MS (EI): calc. for $C_9H_{10}N_4O_4$: 238.0702; obs.: 238.0694.

EXAMPLE 39

Compound E39

To a flame-dried flask, under nitrogen, containing a stirred suspension of compound E37 (500 mg) in distilled THF (10 ml) is added N-methyl-N-(trimethylsilyl)trifluoroacetamide (1.13 ml). In another flame-dried flask, under nitrogen, containing a stirred suspension of 11 (710 mg) in distilled methylene chloride (15 ml), cooled to −10° C., is added chlorosulfonylisocyanate (0.13 ml). After 45 minutes stirring at −10° to 0° C. more chlorosulfonylisocyanate (0.03 ml) is added and the mixture is warmed to room temperature. Both mixtures are cooled to 0° C. and combined. The combined mixture is warmed to room temperature. After 3 hours methanol is added and the mixture is evaporated to dryness to give E39 (1.92 g). Physical characteristics are as follows:

MS (FAB) calc. for $C_{36}H_{43}N_{10}O_{14}S_2$: 903.2401; obs.: 903.2417.

EXAMPLE 40

Compound E40, Acetic acid,
[[[1-(2-amino-4-thiazolyl)-2-[[1-[[[[3-[[(1,4-dihydro-3-hydroxy-4-oxo-2-pyridinyl)carbonyl]amino]-2-oxo-1-imidazolidinyl]sulfonyl]-amino]carbonyl]-2-oxo-3-azetidinyl]amino]-2-oxoethylidene]amino]oxy]-, [S-(Z)]-

A stirred solution E39 (122 mg) in methanol (5 ml) is hydrogenated with palladium black (105 mg) at one atmosphere for 30 minutes. The mixture is then filtered, rinsed with methanol, and evaporated to dryness to give solid. The residue is suspended in methylene chloride (1 ml), cooled to −5° C., and to it is added trifluoroacetic acid (1 ml). The mixture is stirred for 90 minutes under nitrogen at −5°–0° C. then evaporated to dryness. The residue is triturated with cold diethyl ether and filtered. The residue is chromatographed through 50 ml Dianion HP-20 resin, eluting with water (50 ml), 2%, 4%, and 10% acetonitrile/water (50 ml each), and 20% acetonitrile/water (150 ml) to give E40 (25 mg). Physical characteristics are as follows:

MS (FAB) (M·+H)+ at 657 (weak).

EXAMPLE 41

Compound E41, Propanoic acid,
2-[[[2-[[1-[[[[3-[[[1-cyclopropyl-1,4-dihydro-4-oxo-5-(phenylmethoxy)-2-pyridinyl]carbonyl]amino]-2-oxo-1-imidazolidinyl]sulfonyl]amino]carbonyl]-2-oxo-3-azetidinyl]amino]-1-[2-[[(1,1-dimethylethoxy)carbonyl]amino]-4-thiazolyl]-2-oxoethylidene]amino]oxy]-2-methyl-, 1,1-dimethylethyl ester, [S-(Z)]-

To a flame-dried flask, under nitrogen, containing a stirred suspension of compound E37(a) in distilled THF (2 ml) is added N-methyl-N-(trimethylsilyl)trifluoroacetamide (0.20 ml). The solids dissolve in about 20 minutes. To another flame-dried flask, under nitrogen, containing a stirred suspension of 11 (134 mg) in distilled methylene chloride (2 ml) cooled to −5° C., is added chlorosulfonylisocyanate (0.030 ml). After 30 minutes at 0° C. additional CSI (0.005 ml) is added. After 5 minutes, the two solutions are combined at 0° C. The combined mixture is stirred for 2 hours 45 minutes at 0° C., then for one hour 15 minutes at room temperature. The mixture is then evaporated to give compound E41 (325 mg). Physical characteristics are as follows:

MS (FAB) calc. for $C_{41}H_{51}N_{10}O_{14}S_2$: 971.3027; obs.: 971.3041.

According to the procedure of Example 41, the following compounds are also prepared:

Compound E41(a), Propanoic acid, 2-[[[2-[[1-[[[[3-[[[1,4-dihydro-1-methyl 4-oxo-5-(phenylmethoxy)-2-pyridinyl]carbonyl]amino]-2-oxo-1-imidazolidinyl]sulfonyl]amino]carbonyl]2-oxo-3-azetidinyl]amino]-1-[2-[[(1,1-dimethylethoxy)carbonyl]amino]-4-thiazolyl]-2-oxoethylidene]amino]oxy]-2-methyl-, 1,1 dimethylethyl ester, [S-(Z)]-, Compound E41(b), Propanoic acid, 2-[[[2-[[1-[[[[3-[[[-1-butyl-1,4-dihydro-4-oxo-5-(phenylmethoxy)-2-pyridinyl]carbonyl]amino]-2-oxo-1-imidazolidinyl]sulfonyl]amino]carbonyl]-2-oxo-3-azetidinyl]. -amino]-1-[2-[[(1,1-dimethylethoxy)carbonyl]amino]-4-thiazolyl]-2-oxoethylidene]amino]oxy]-2-methyl-, 1,1-dimethylethyl ester, [S-(Z)]-, Compound E41(c), Propanoic acid, 2-[[[2-[[1-[[[[3-[[(1,6-dihydro-1-hydroxy-2-oxo-6-pyridinyl)carbonyl]amino]-2-oxo-1-imidazolidinyl]sulfonyl]amino]carbonyl]-2-oxo-3-azetidinyl]amino]1-[2-[[(1,1-dimethylethoxy)carbonyl]amino]-4-thiazolyl]-2-oxoethylidene]aminoJoxyl-2-methyl-, 1,1-dimethylethyl ester, [S-(Z)]-.

Physical characteristics are as follows:

MS (FAB) (M·+H)+ calc. for $C_{31}H_{41}N_{10}O_{14}S_2$: 841.2245; obs.: 841.2220.

Compound E41(d), Propanoic acid, 2-[[[2-[[1-[[[[3-[[(1,2-dihydro-1-hydroxy-2-oxo-4-pyridinyl)carbonyl]amino]-2-oxo-1-imidazolidinyl]sulfonyl]amino]carbonyl]-2-oxo-3-azetidinyl]amino]-1-[2-[[(1,1-dimethylethoxy)carbonyl]amino]-4-thiazolyl]-2-oxoethylidene]amino]oxy]-2-methyl-, 1,1-dimethylethyl ester, [S-(Z)]- .

Physical characteristics are as follows:

MS (FAB) (M·+H)+ calc. for $C_{31}H_{41}N_{10}O_{14}S_2$: 841.2245., obs.: 841.2247.

Compound E41(e), Propanoic acid, 2-[[[2-[[1-[[[[3-[[(1,2-dihydro-1-hydroxy-2-oxo-5-pyridinyl)carbonyl]amino]-2-oxo-1-imidazolidinyl]sulfonyl]amino]carbonyl]-2-oxo-3-azetidinyl]amino]1 [2-[[(1,1-dimethylethoxy)carbonyl]amino]-4-thiazolyl]-2-oxoethylidene]amino]oxy]-2-methyl-, 1,1-dimethylethyl ester, [S-(Z)]-.

Physical characteristics are as follows:

MS (FAB) (M·+H)+ calc. for $C_{31}H_{41}N_{10}O_{14}S_2$: 841.2245; obs.: 841.2262.

EXAMPLE 42

Compound E42, Propanoic acid, 2-[[[1-(2-amino-4-thiazolyl)-2-[[1-[[[[3-[[(1-cyclopropyl-1,4-dihydro-5-hydroxy-4-oxo-2-pyridinyl)carbonyl-]amino]-2-oxo-1-imidazolidinyl]sulfonyl]amino]carbonyl]-2-oxo-3-azetidinyl]amino]-2-oxoethylidene]amino]oxy]-2-methyl-, [S-(Z)]-

A stirred solution of 200 mg of propanoic acid, 2-[[[2-[[1-[[[[3[[[1,4-dihydro-1-cyclopropyl-4-oxo-5-(phenyl methoxy)-2-pyridinyl]carbonyl]amino]2-oxo-1-im idazolidinyl]sulfonyl]amino]carbonyl]2-oxo-3-azetidinyl]amino]-1-[2-[[1,1-dimethylethoxy)carbonyl-]amino]-4-thiazolyl]-2-oxoethylidene]amino]oxy]-2-methyl-, 1,1 dimethylethyl ester, [S(Z)]- in methanol (10 ml) is stirred under one atmosphere of hydrogen in the presence of palladium black (200 mg) for one hour. The palladium is then filtered off and the filtrate evaporated to dryness. The residue is dissolved in methylene chloride (2 ml), cooled to 0° C., and treated with trifluoroacetic acid (2 ml). The cooling bath is removed and the mixture stirred at room temperature, under nitrogen, for one hour. The mixture is evaporated to dryness and the residue triturated with diethyl ether and filtered. The crude product is chromatographed through 100 ml Diaion HP-20 resin to give compound E42.

Physical characteristics are as follows:
MS (FAB) (M·+H)+ calc. for $C_{25}H_{29}N_{10}O_{12}S_2$: 725.1408; obs.: 725.1409.

According to the procedure of Example 21, the following compounds are also prepared:

Compound E42(a), Propanoic acid, 2-[[[1-(2-amino-4-thiazolyl)-2-[[1-[[[[3-[[(1,4-dihydro-5-hydroxy-1-methyl-4-oxo-2 pyridinyl)carbonyl]amino]-2-oxo-1-imidazolidinyl]sulfonyl]amino]carbonyl]-2-oxo-3-azetidinyl]amino]-2-oxoethylidene]amino]oxyl-2-methyl-, [S-(Z)]-.

Physical characteristics are as follows:
MS (EI), parent 698.

Compound E42(b), Propanoic acid, 2-[[[1-(2-amino--4-thiazolyl)-2-[[1-[[[[3-[[(1-butyl-1,4-dihydro-5-hydroxy-4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methyl-, [S-(Z)]-.

Physical characteristics are as follows:
MS (FAB) (M·+H)+ calc. for $C_{26}H_{33}N_{10}O_{12}S_2$: 741.1721; obs.: 741.1755.

Compound E42(c), Propanoic acid, 2-[[[1-(2-amino-4-thiazolyl)-2[[1-[[[[3-[[(1,6-dihydro-1-hydroxy-2-oxo-6-pyridinyl)carbonyl]amino]- 2-oxo-1-imidazolidinyl]sulfonyl]amino]carbonyl]-2-oxo-3-azetidinyl]-amino]-2-oxoethylidene]amino]oxy]-2-methyl-, [S-(Z)]-.

Physical characteristics are as follows:
MS (FAB) (M·+H)+ calc. for $C_{22}H_{25}N_{10}O_{12}S_2$: 685.1095, obs.: 685.1095.

Compound E42(d), Propanoic acid, 2-[[[1-(2-amino-4-thiazolyl)-2-[[1-[[[[3-[[(1,2-dihydro-1-hydroxy-2-oxo--4-pyridinyl)carbonyl]amino]2-oxo-1-imidazolidinyl]sulfonyl]amino]carbonyl]-2-oxo-3-azetidinyl]amino]-2-oxoethylidene]amino]oxy]-2-methyl-, [S-(Z)]-.

Physical characteristics are as follows:
MS (FAB) (M·+H)+ calc. for $C_{22}H_{25}N_{10}O_{12}S_2$: 685.1095; obs.: 685.1127.

Compound E42(e), Propanoic acid, 2-[[[1-(2-amino-4-thiazolyl)-2-[[1-[[[[3-[[(1,2-dihydro-1-hydroxy-2-oxo-5-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methyl-, [S-(Z)]-.

Physical characteristics are as follows:
MS (FAB) (M·+H)+ calc. for $C_{22}H_{25}N_{10}O_{12}S_2$: 685.1095; obs.: 685.1106.

FORMULAS

FORMULAS

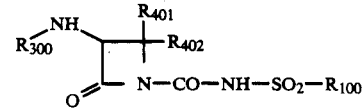

Formula 1

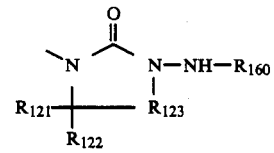

Formula 2

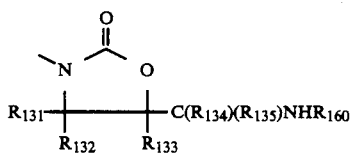

Formula 3

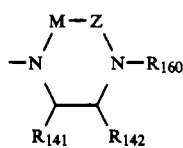

Formula 4

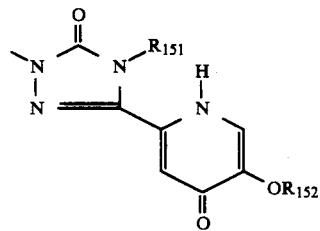

Formula 5

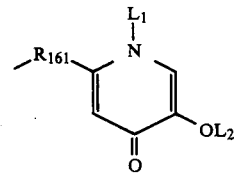

Formula 6

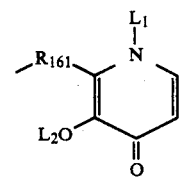

Formula 7

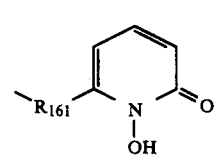

Formula 8

-continued
FORMULAS

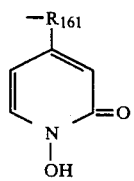 Formula 9

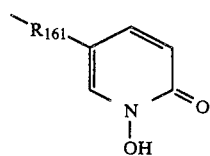 Formula 10

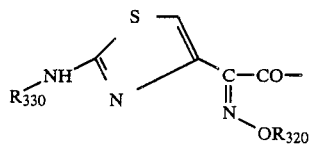 Formula 11

STRUCTURE CHART

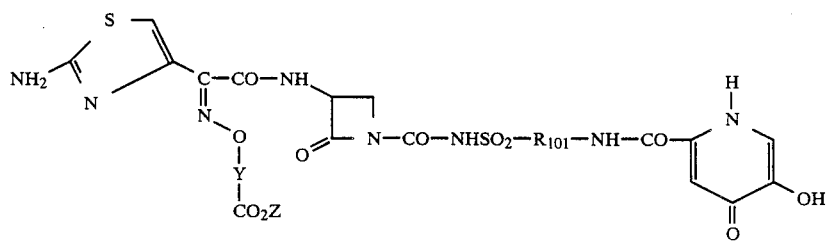

| Compound Number | Y | $R_{101}$ |
|---|---|---|
| E11 | $\underset{|}{\overset{|}{C(CH_3)_2}}$ | hydantoin-like ring (−N−C(=O)−N−CH$_2$−C(=O)−) |
| E17 | $\underset{|}{\overset{|}{C(CH_3)_2}}$ | 2-oxopiperazine (−N−C(=O)−CH$_2$−N−) |
| E18 | $\underset{|}{\overset{|}{C(CH_3)_2}}$ | 3-oxo-hexahydro-1,2,4-triazine |
| E19 | $\underset{|}{\overset{|}{CH_2}}$ | piperazine (−N−...−N−) |
| E27(a) | $\underset{|}{\overset{|}{CH_2}}$ | 2-oxo-oxazolidine |
| E27(b) | $\underset{|}{\overset{|}{C(CH_3)_2}}$ | 2-oxo-oxazolidine |

-continued
STRUCTURE CHART
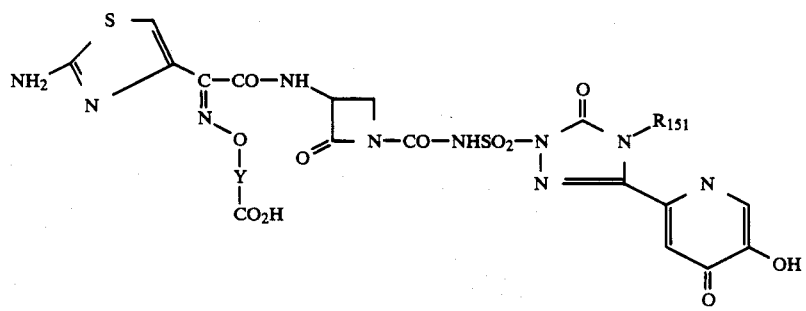
| Compound Number | Y | $R_{151}$ |
|---|---|---|
| E23(a) | $-C(CH_3)_2-$ | H |
| E23(b) | $-C(CH_3)_2-$ | Me |
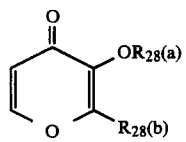
| Compound Number | $R_{28}(a)$ | $R_{28}(b)$ |
|---|---|---|
| E28(a) | $-H$ | $-CH_2OCO(C_6H_5)$ |
| E28(b) | $-CH_2(C_6H_5)$ | $-CH_2OCO(C_6H_5)$ |
| E29 | $-CH_2(C_6H_5)$ | $-CH_2OH$ |
| E30 | $-CH_2(C_6H_5)$ | $-CO_2H$ |
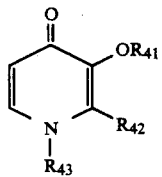
| Compound Number | $R_{41}$ | $R_{42}$ | $R_{43}$ |
|---|---|---|---|
| E31 | $-CH_2-(C_6H_5)$ | $CO_2H$ | H |
| E37 | $-CH_2-(C_6H_5)$ | $HN\underset{\underset{O}{\parallel}}{\diagdown}N-NH-CO-$ | H |
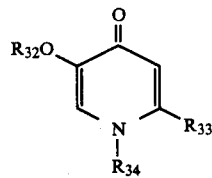
| Compound Number | $R_{32}$ | $R_{33}$ | $R_{34}$ |
|---|---|---|---|
| E32 | $-CH_2-(C_6H_5)$ | $-CO_2H$ | cyclopropyl |
| E33 | $-CH_2-(C_6H_5)$ | $-CO_2H$ | $-CH_3$ |

4,975,538
-continued
STRUCTURE CHART
| | | | |
|---|---|---|---|
| E37(a) | —CH₂—(C₆H₅) | 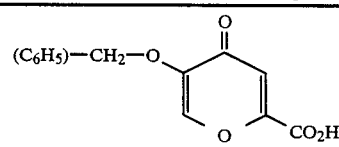 | 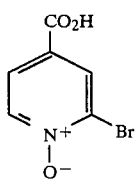 |
| E38 | —CH₂—(C₆H₅) | 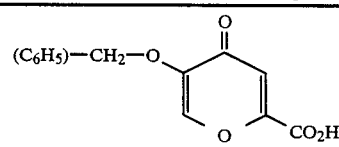 | —CH₃ |
| E38(a) | —CH₂—(C₆H₅) | 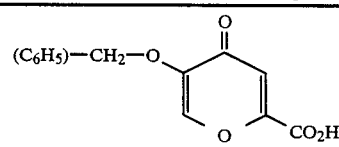 | —CH₂(CH₂)₂CH₃ |
| E34 | —CH₂—(C₆H₅) | —CO₂H | —CH₂(CH₂)₂CH₃ |
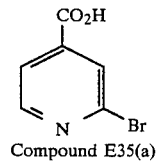
Compound E33(a)
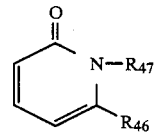
Compound E35
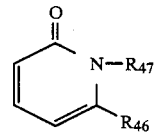
Compound E35(a)
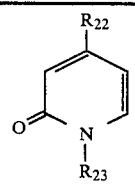
| Compound Number | $R_{46}$ | $R_{47}$ |
|---|---|---|
| E37(b) | 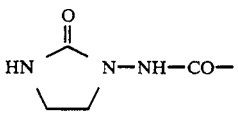 | —OH |
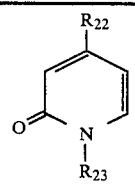
| Compound Number | $R_{22}$ | $R_{23}$ |
|---|---|---|
| E36 | —CO₂H | —OH |
| E38(b) | 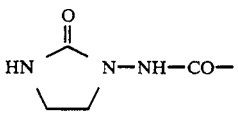 | —OH |

-continued
STRUCTURE CHART
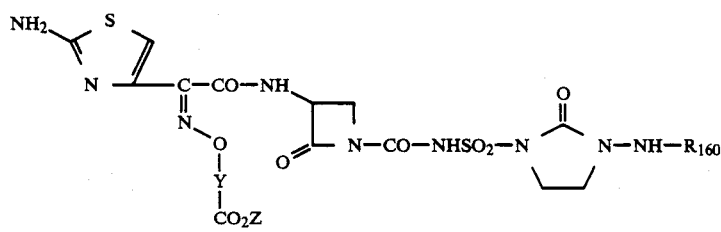
| Compound Number | Y | Z | R160 |
|---|---|---|---|
| E39 | −CH2− | (CH3)3C− | (C6H5)−CH2−O− pyridinone −CO− |
| E40 | −CH2− | H | HO− pyridinone −CO− |
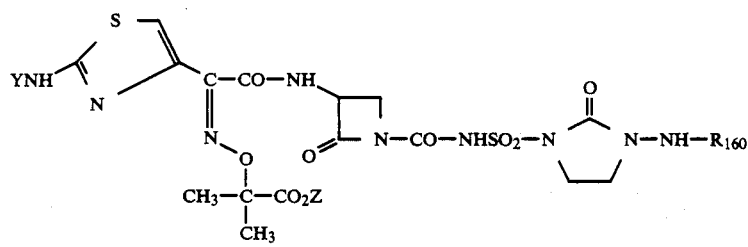
| Compound Number | Y | Z | R160 |
|---|---|---|---|
| E41 | (CH3)3CO2C− | (CH3)3C− | (C6H5)−CH2−O− N-cyclopropyl pyridinone −CO− |
| E42 | H | H | HO− N-cyclopropyl pyridinone −CO− |
| E41(a) | (CH3)3CO2C− | (CH3)3C− | (C6H5)−CH2−O− N-CH3 pyridinone −CO− |

CHART A -continued
STRUCTURE CHART
| | | | |
|---|---|---|---|
| E42(a) | H | H | 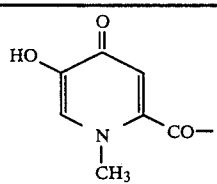 |
| E41(b) | (CH₃)₃CO₂C— | (CH₃)₃C— | 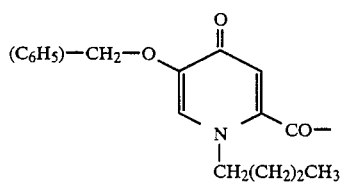 |
| E42(b) | H | H | 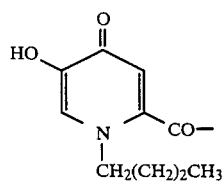 |
| E41(c) | (CH₃)₃CO₂C— | (CH₃)₃C— | 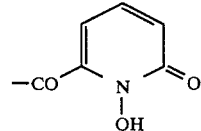 |
| E42(c) | H | H | 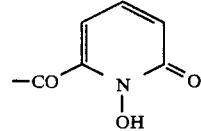 |
| E41(d) | (CH₃)₃CO₂C— | (CH₃)₃C— | 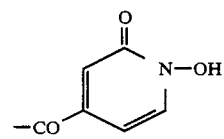 |
| E42(d) | H | H | 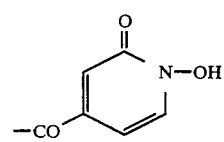 |
| E41(e) | CH₃)₃CO₂C— | (CH₃)₃C— | 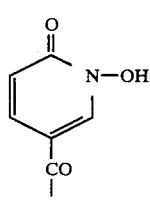 |
| E42(e) | H | H | 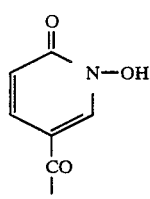 |

CHART A
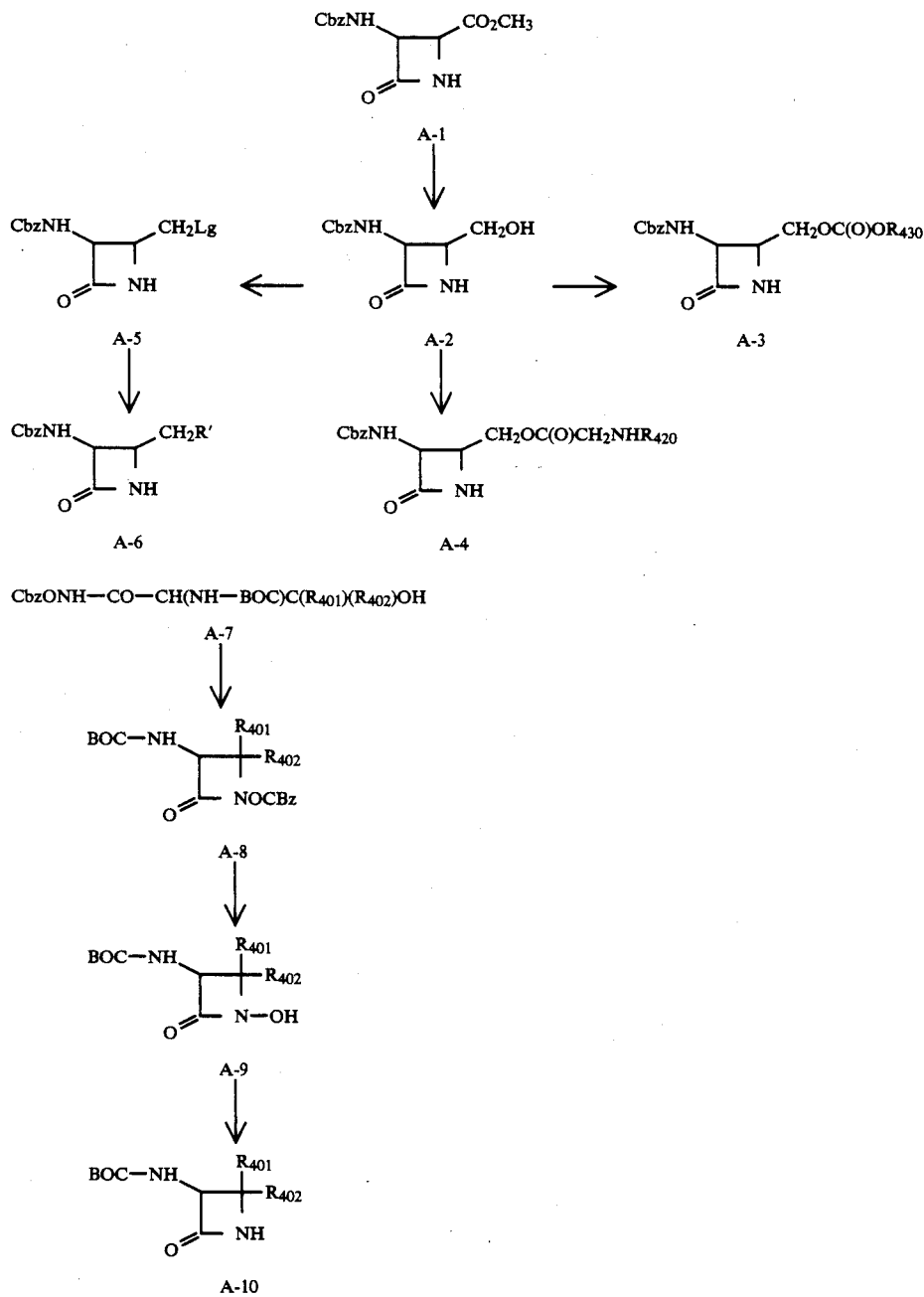
CHART B

-continued
CHART B
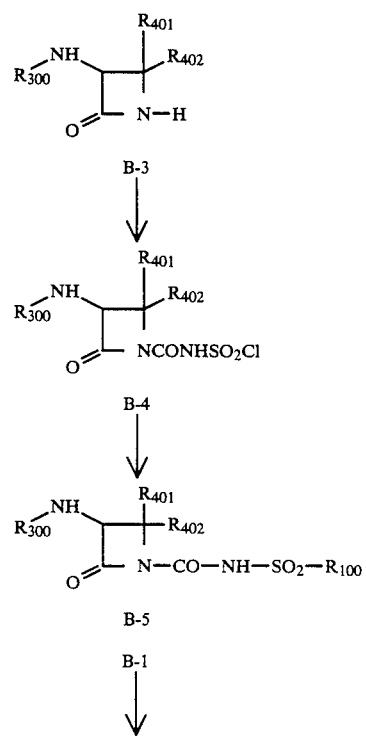
-continued
CHART B
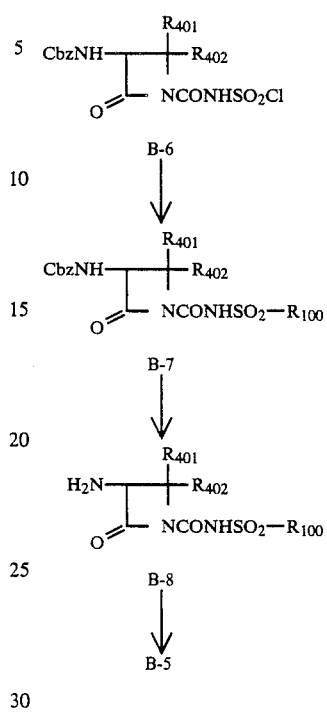
CHART C
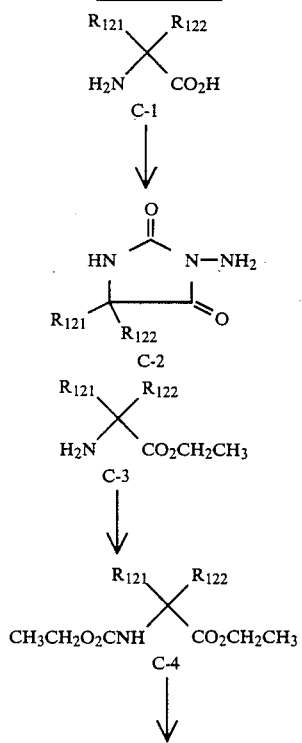

CHART C
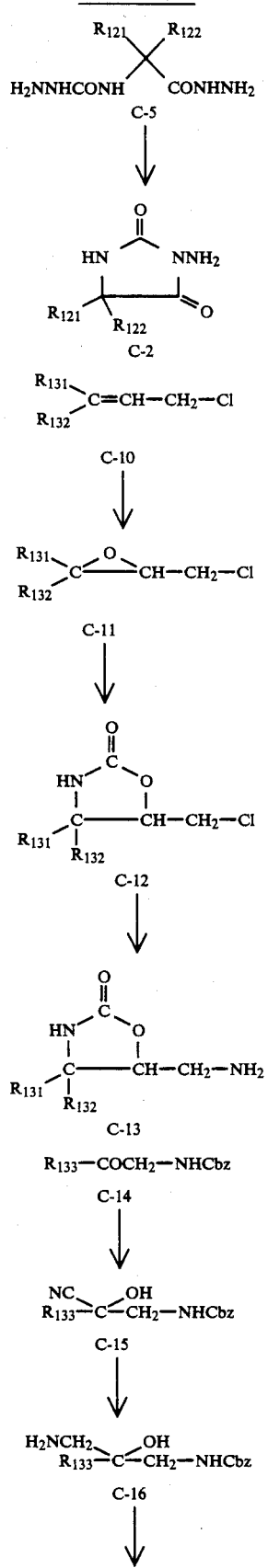

CHART C -continued
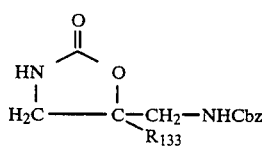
↓ C-17
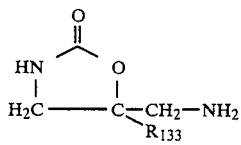
C-18
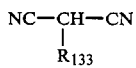
↓ C-19
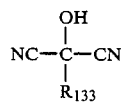
C-20
↓
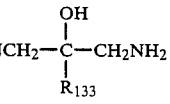
C-21
↓
C-18
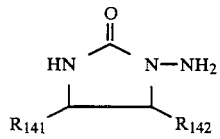
C-30
↓
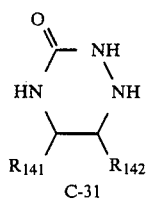
C-31

-continued
CHART C
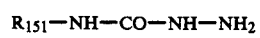
C-40
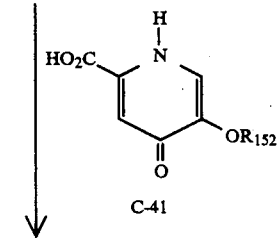
C-41
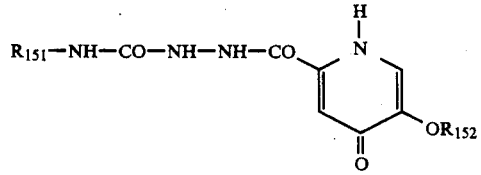
C-42
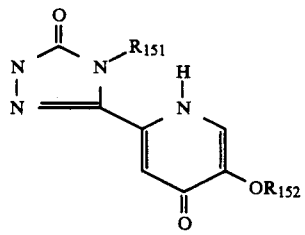
C-43
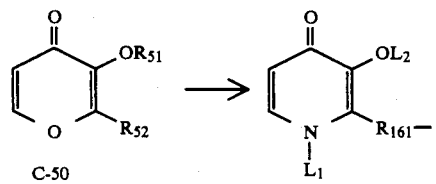
C-50
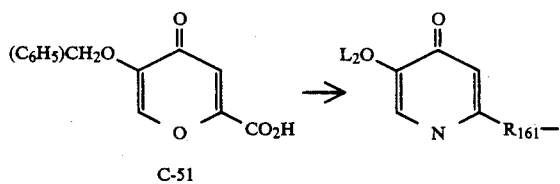
C-51
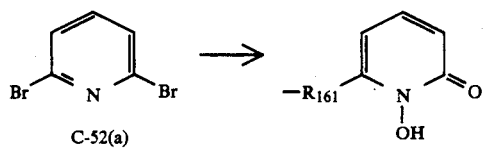
C-52(a)
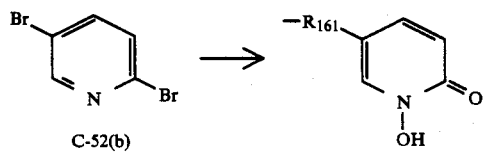
C-52(b)

-continued

CHART C

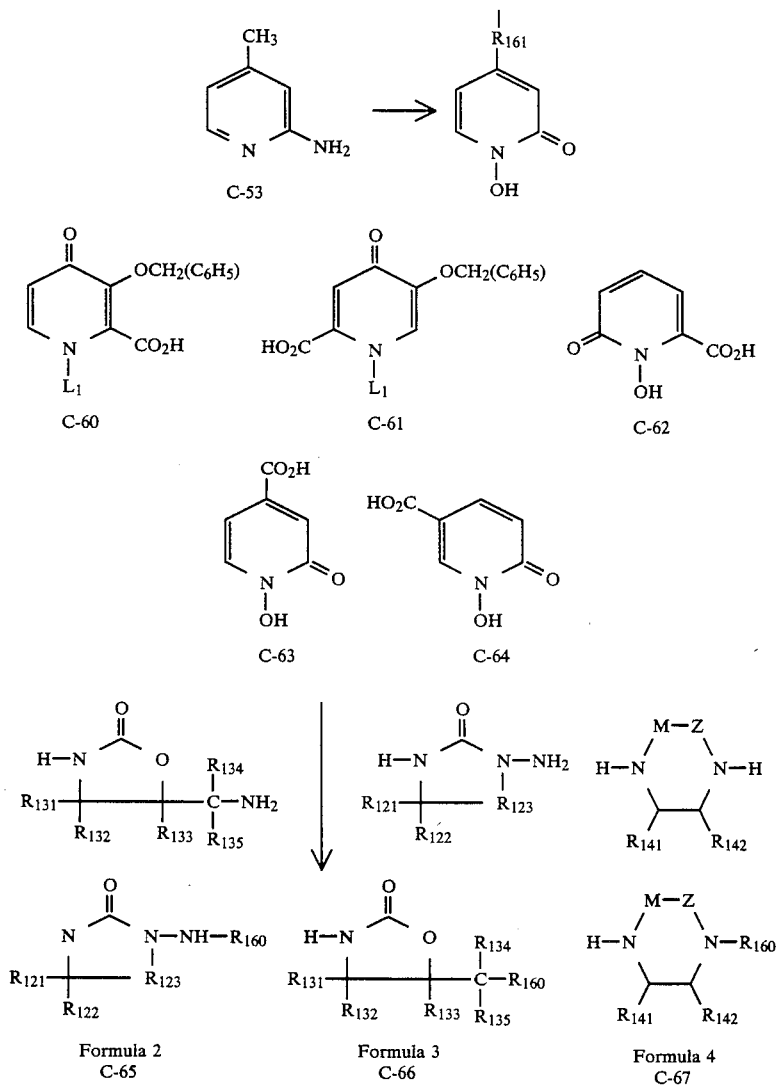

| TABLE I | | |
|---|---|---|
| Organism | Culture Number | Compound E11 |
| Minimum Inhibitory Concentration (mcg/ml) | | |
| Staphylococcus Aureus | 9218 | 64 |
| Staphylococcus Aureus | 3665 | >64 |
| Staphylococcus Aureus | 6685 | >64 |
| Streptococcus Faecalis | 694 | >64 |
| Streptococcus Pneumoniae | 41 | >64 |
| Streptococcus Pyogenes | 152 | 64 |
| Citrobacter Freundli | 3507 | 0.5 |
| Enterobacter Cloacae | 9381 | >64 |
| Enterobacter Cloacae | 9382 | 2 |
| Escherichia Coli | 9379 | 0.03 |
| Escherichia Coli | 9380 | 0.015 |
| Escherichia Coli | 9451 | 0.06 |
| Klebsiella Oxytoca | 9383 | 0.5 |
| Klebsiella Oxytoca | 9384 | 0.125 |
| Klebsiella Pneumoniae | 58 | 1 |
| Proteus Vulgaris | 9679 | 0.5 |
| Serratia Marcescens | 6888 | 0.125 |
| Pseudomonas Aeruginosa | 231 | 0.5 |
| Pseudomonas Aeruginosa | 9191 | 0.5 |
| Organism | Culture Number | Compound E17 |

| TABLE I-continued | | |
|---|---|---|
| Staphylococcus Aureus | 9218 | >64 |
| Staphylococcus Aureus | 3665 | >64 |
| Staphylococcus Aureus | 6685 | >64 |
| Streptococcus Faecalis | 694 | >64 |
| Streptococcus Pneumoniae | 41 | >64 |
| Streptococcus Pyogenes | 152 | 16 |
| Citrobacter Freundli | 3507 | 0.25 |
| Enterobacter Cloacae | 9381 | 64 |
| Enterobacter Cloacae | 9382 | 1 |
| Escherichia Coli | 9379 | 0.015 |
| Escherichia Coli | 9380 | <0.008 |
| Escherichia Coli | 9451 | 0.015 |
| Klebsiella Oxytoca | 9383 | 0.5 |
| Klebsiella Oxytoca | 9384 | 0.125 |
| Klebsiella Pneumoniae | 58 | 1 |
| Proteus Vulgaris | 9679 | 0.25 |
| Serratia Marcescens | 6888 | 0.125 |
| Pseudomonas Aeruginosa | 231 | 0.5 |
| Pseudomonas Aeruginosa | 9191 | 0.5 |
| Organism | Culture Number | Compound E18 |
| Staphylococcus Aureus | 9218 | >64 |
| Staphylococcus Aureus | 3665 | >64 |
| Staphylococcus Aureus | 6685 | >64 |
| Streptococcus Faecalis | 694 | >64 |

TABLE I-continued

| Organism | Culture Number | MIC |
|---|---|---|
| Streptococcus Pneumoniae | 41 | >64 |
| Streptococcus Pyogenes | 152 | 16 |
| Citrobacter Freundli | 3507 | 0.06 |
| Enterobacter Cloacae | 9381 | 16 |
| Enterobacter Cloacae | 9382 | 1 |
| Escherichia Coli | 9379 | <0.008 |
| Escherichia Coli | 9380 | <0.008 |
| Escherichia Coli | 9451 | <0.008 |
| Klebsiella Oxytoca | 9383 | 0.125 |
| Klebsiella Oxytoca | 9384 | 0.03 |
| Klebsiella Pneumoniae | 58 | 0.5 |
| Proteus Vulgaris | 9679 | 0.06 |
| Serratia Marcescens | 6888 | 0.06 |
| Pseudomonas Aeruginosa | 231 | 0.25 |
| Pseudomonas Aeruginosa | 9191 | 0.125 |

| Organism | Culture Number | Compound E19 |
|---|---|---|
| *Minimum Inhibitory Concentration (μg/ml)* | | |
| Staphylococcus Aureus | 9218 | >128 |
| Staphylococcus Aureus | 3665 | >128 |
| Staphylococcus Aureus | 6685 | >128 |
| Streptococcus Faecalis | 694 | >128 |
| Streptococcus Pneumoniae | 41 | >128 |
| Streptococcus Pyogenes | 152 | 64 |
| Citrobacter Freundli | 3507 | 2 |
| Enterobacter Cloacae | 9381 | 128 |
| Enterobacter Cloacae | 9382 | 16 |
| Escherichia Coli | 9379 | 0.25 |
| Escherichia Coli | 9380 | 0.06 |
| Escherichia Coli | 9451 | 0.125 |
| Klebsiella Oxytoca | 9383 | 64 |
| Klebsiella Oxytoca | 9384 | 0.5 |
| Klebsiella Pneumoniae | 58 | 8 |
| Proteus Vulgaris | 9679 | 4 |
| Serratia Marcescens | 6888 | 1 |
| Pseudomonas Aeruginosa | 231 | 8 |
| Pseudomonas Aeruginosa | 9191 | 8 |

| Organism | Culture Number | Compound E23 (a) | Compound E23 (b) |
|---|---|---|---|
| Staphylococcus Aureus | 9218 | >64 | >64 |
| Staphylococcus Aureus | 3665 | >64 | >64 |
| Staphylococcus Aureus | 6685 | >64 | >64 |
| Streptococcus Faecalis | 694 | >64 | >64 |
| Streptococcus Pneumoniae | 41 | >64 | >64 |
| Streptococcus Pyogenes | 152 | 16 | 16 |
| Citrobacter Freundli | 3507 | 0.03 | 0.03 |
| Enterobacter Cloacae | 9381 | 4 | 4 |
| Enterobacter Cloacae | 9382 | 0.5 | 0.5 |
| Escherichia Coli | 9379 | <0.008 | <0.008 |
| Escherichia Coli | 9380 | <0.008 | <0.008 |
| Escherichia Coli | 9451 | <0.008 | <0.008 |
| Klebsiella Oxytoca | 9383 | 0.03 | 0.03 |
| Klebsiella Oxytoca | 9384 | 0.03 | 0.03 |
| Klebsiella Pneumoniae | 58 | 0.25 | 0.25 |
| Proteus Vulgaris | 9679 | 0.03 | 0.03 |
| Serratia Marcescens | 6888 | 0.015 | 0.015 |
| Pseudomonas Aeruginosa | 231 | 0.5 | 0.125 |
| Pseudomonas Aeruginosa | 9191 | 0.5 | 0.25 |

| Organism | Culture Number | Compound E27 (a) | Compound E27 (b) |
|---|---|---|---|
| S. pyogenes | 152 | 16 | 64 |
| C. freundii | 3507 | 0.25 | 0.5 |
| E. cloacae | 9381 | 128 | 128 |
| E. cloacae | 9382 | 2 | 8 |
| E. coli | 9379 | <0.06 | 0.125 |
| E. coli | 9380 | <0.06 | 0.03 |
| E. coli | 9451 | <0.06 | 0.06 |
| K. oxytoca | 9383 | 4 | 4 |
| K. oxytoca | 9384 | 0.25 | 0.25 |
| K. pneumoniae | 58 | 0.5 | 2 |
| P. vulgaris | 9679 | 0.5 | 0.5 |
| S. marcescens | 9888 | 0.5 | 0.5 |
| Ps. aeruginosa | 231 | 4 | 4 |
| Ps. aeruginosa | 9191 | 64 | 8 |

| Organism | Culture Number | Compound E40 | Compound E42 (c) | Compound E42 (d) |
|---|---|---|---|---|
| Staphylococcus aureus | 9218 | >64 | >64 | >64 |
| Staphylococcus aureus | 3665 | >64 | >64 | >64 |
| Staphylococcus aureus | 6685 | >64 | >64 | >64 |
| Staphylococcus aureus | 9213 | >64 | — | — |
| Staphylococcus epidermidis | 30031 | >64 | — | — |
| Streptococcus faecalis | 694 | >64 | >64 | >64 |
| Streptococcus pneumoniae | 41 | >64 | >64 | 64 |
| Streptococcus pyogenes | 152 | 64 | 4 | 4 |
| Citrobacter freundli | 3507 | 0.25 | 0.5 | 0.25 |
| Enterobacter cloacae | 9381 | 64 | >64 | 64 |
| Enterobacter cloacae | 9382 | 1 | 1 | 0.5 |
| Escherichia coli | 9379 | 0.5 | 0.25 | 0.25 |
| Escherichia coli | 9380 | 1 | 0.25 | 0.25 |
| Escherichia coli | 9451 | 0.5 | 0.5 | 0.125 |
| Klebsiella oxytoca | 9383 | 2 | 8 | 4 |
| Klebsiella oxytoca | 9384 | 0.5 | 0.5 | 0.25 |
| Klebsiella pneumoniae | 58 | 0.5 | 0.5 | 0.25 |
| Proteus vulgaris | 9679 | 0.25 | 0.06 | 0.03 |
| Serratia marcescens | 6888 | 2 | 0.5 | 0.5 |
| Pseudomonas aeruginosa | 231 | 64 | 4 | 1 |
| Pseudomonas aeruginosa | 9191 | 64 | 8 | 1 |

| Organism | Culture Number | Compound E42 (a) | Compound E42 | Compound E42 (b) |
|---|---|---|---|---|
| Staphylococcus aureus | 9218 | >128 | >64 | >64 |
| Staphylococcus aureus | 3665 | >128 | >64 | >64 |
| Staphylococcus aureus | 6685 | >128 | >64 | >64 |
| Streptococcus faecalis | 694 | >128 | >64 | >64 |
| Streptococcus pneumoniae | 41 | >128 | >64 | >64 |
| Streptococcus pyogenes | 152 | 128 | 64 | 16 |
| Citrobacter freundli | 3507 | 0.5 | 0.5 | 2 |
| Enterobacter cloacae | 9381 | 64 | 64 | >64 |
| Enterobacter cloacae | 9382 | 4 | 4 | 1 |
| Escherichia coli | 9379 | 0.06 | 0.06 | 0.5 |
| Escherichia coli | 9380 | <0.015 | 0.03 | 0.25 |
| Escherichia coli | 9451 | 0.06 | 0.125 | 0.5 |
| Klebsiella oxytoca | 9383 | 1 | 1 | 4 |
| Klebsiella oxytoca | 9384 | 0.5 | 0.5 | 0.25 |
| Klebsiella pneumoniae | 58 | 2 | 2 | 0.5 |
| Proteus vulgaris | 9679 | 0.5 | 2 | 0.25 |
| Serratia marcescens | 6888 | 0.25 | 0.5 | 1 |
| Pseudomonas aeruginosa | 231 | 2 | 16 | >64 |
| Pseudomonas aeruginosa | 9191 | 2 | 16 | 64 |

We claim:
1. A compound of Formula 1,

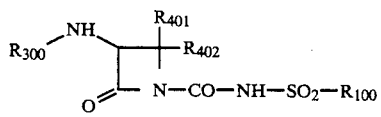

Formula 1 and pharmaceutically acceptable salts thereof; wherein $R_{401}$ and $R_{402}$ are the same or different and are
(a) hydrogen,
(b) $(C_1-C_{12})$ alkyl
(c) $(C_2-C_8)$ alkenyl,
(d) $(C_2-C_8)$ alkynyl,
(e) $(C_3-C_{10})$ cycloalkyl,
(f) phenyl optionally substituted with from one to 3 substituents selected from the group consisting of halogen, hydroxy, amino, nitro, $(C_1-C_4)$alkyl, and $(C_1-C_4)$alkoxy,
(g) benzyl optionally substituted with from one to 3 substituents selected from the group consisting of halogen, hydroxy, amino, nitro, $(C_1-C_4)$alkyl, and $(C_1-C_4)$alkoxy,
(h) $-CH_2-O-CO-CH_2NHR_{420}$,
(i) $-CH_2O-CO_2-R_{430}$,
(j) $-CH_2F$, or
(k) $-CHF_2$;
wherein $R_{420}$ is
(a) hydrogen,
(b) $-COH$, or
(c) $-CO-O-C(CH_3)_3$;
wherein $R_{430}$ is $(C_1-C_8)$alkyl, $-(CH_2)_2OC(O)NH_2$, $-(CH_2)_2Cl$, $-(CH_2)_2OCH_3$ or $-(CH_2)_2NHCOH$;
wherein $R_{300}$ is an acyl group derived from a carboxylic acid; wherein $R_{100}$ is a heterocyclic compound of Formula 2, 3, 4 or 5;

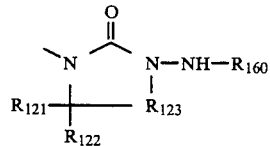

Formula 2

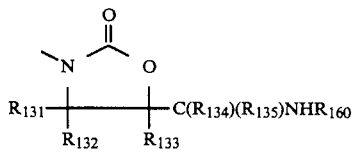

Formula 3

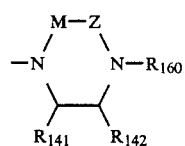

Formula 4

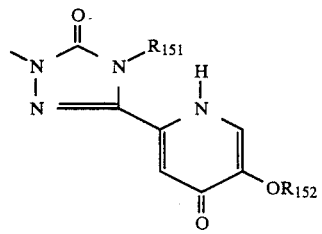

Formula 5 wherein $R_{121}$ and $R_{122}$ are hydrogen;
wherein $R_{123}$ is methylene or carbonyl;
wherein $R_{131}$ and $R_{132}$ are hydrogen or $(C_1-C_3)$ alkyl with the proviso that if one of $R_{131}$ or $R_{132}$ is alkyl the other is hydrogen;
wherein $R_{133}$, $R_{134}$ and $R_{135}$ are the same or different and are
a) hydrogen,
(b) $(C_1-C_3)$ alkyl,
(c) $(C_3-C_4)$ cycloalkyl, or
(d) phenyl with the proviso that if one of $R_{134}$ or $R_{135}$ are $(C_1-C_3)$ alkyl, $(C_3-C_4)$ cycloalkyl, or phenyl the other is hydrogen;
wherein $R_{141}$ and $R_{142}$ are the same or different and are
(a) hydrogen,
(b) $(C_1-C_4)$ alkyl,
(c) $(C_2-C_3)$ alkenyl,
(d) $(C_3-C_6)$ cycloalkyl, or
(e) phenyl;
wherein groups b, c, d and e may be substituted by one to 2 substituents selected from the group consisting of halogen, hydroxy, amino, nitro, $(C_1-C_4)$alkyl, and $(C_1-C_4)$alkoxy;
wherein M is carbonyl or methylene;
wherein Z is NH or $C(R_{143})(R_{144})$;
wherein $R_{143}$ and $R_{144}$ are the same or different and are
(a) hydrogen,
(b) $(C_1-C_4)$ alkyl,
(c) $(C_2-C_3)$ alkenyl,
(d) $(C_3-C_6)$ cycloalkyl, or
(e) phenyl;
wherein $R_{151}$ is
(a) hydrogen,
(b) $(C_1-C_4)$ alkyl,
(c) $(C_3-C_6)$ cycloalkyl,
(d) phenyl, or
(e) $-CF_3$;
wherein groups b, c and d may be substituted by one to 2 substituents selected from the group consisting of halogen, hydroxy, amino, nitro, $(C_1-C_4)$alkyl, and $(C_1-C_4)$alkoxy; and
wherein $R_{152}$ is hydrogen or $-CH_2(C_6H_5)$;
wherein $R_{160}$ is a pyridinone of Formula 6, 7, 8, 9, or 10;

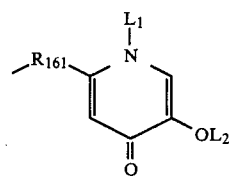

Formula 6

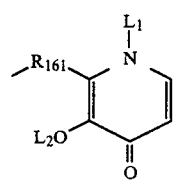

Formula 7

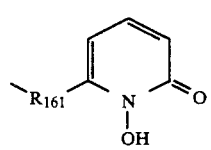

Formula 8

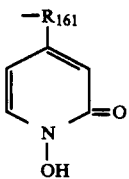

Formula 9

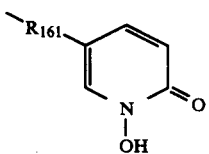

Formula 10 wherein $L_1$ is
(a) hydrogen,
(b) ($C_1$–$C_4$) alkyl,
(c) ($C_2$–$C_3$) alkenyl,
(d) ($C_3$–$C_6$) cycloalkyl,
(e) phenyl, or
(f) —$CF_3$;
wherein groups b, c, d and e may be substituted by one to 2 substituents selected from the group consisting of halogen, hydroxy, amino, nitro, ($C_1$–$C_4$)alkyl, and ($C_1$–$C_4$)alkoxy;
wherein $L_2$ is hydrogen or —$CH_2(C_6H_5)$; and
wherein $L_{161}$ is carbonyl with the proviso that when $R_{100}$ is a heterocyclic compound of Formula 2, $R_{121}$ and $R_{122}$ are hydrogen, $R_{123}$ is methylene and $R_{160}$ is a pyridone of Formula 6 then $L_1$ and $L_2$ are not hydrogen.

2. A compound of claim 1 wherein $R_{300}$ is an oximinoacyl moiety of Formula 11,

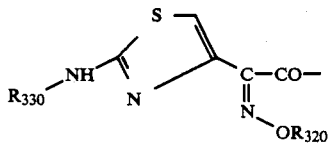

Formula 11 wherein $R_{320}$ is
(a) —$CH_3$,
(b) —$CH_2CO_2R_{321}$,
(c) —$C(CH_3)_2CO_2R_{321}$,
(d) —$CH(CH_3)CO_2R_{321}$,
(e) —$C(CH_2)CO_2R_{321}$,
(f) —X—$CO_2R_{321}$,
(g) —$CH_2CONHOH$, or
(h) —$C(CH_3)_2CONHOH$;
wherein X is

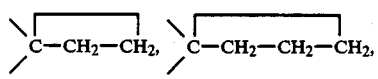

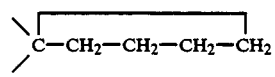

wherein $R_{321}$ is
(a) hydrogen,
(b) ($C_1$–$C_4$) alkyl,
(c) —$CH(C_6H_5)_2$,
(d) —$CH_2(C_6H_5)$, or
(e) a cation;
wherein $R_{330}$ is
(a) hydrogen,
(b) —CO—O—$C(CH_3)_3$,
(c) —CO—O—$CH_2$—$(C_6H_5)$, or
(d) —$C(C_6H_5)_3$.

3. A compound of claim 2; wherein $R_{401}$ and $R_{402}$ are hydrogen, wherein $R_{321}$ is hydrogen, ($C_1$–$C_4$) alkyl or a cation, and wherein $R_{330}$ is hydrogen.

4. A compound of claim 3; wherein $R_{100}$ is a heterocyclic compound of Formula 2.

5. A compound of claim 4; which is 2-[[[1-[2-[[(1,1-dimethylethoxy)carbonyl]amino]-4-thiazolyl]-2-[[1-[[[[3-[[(1,4-dihydro-4-oxo-5-hydroxy-2-pyridinyl)-carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 1,1-dimethylethyl ester; 2-[[[1-(2-amino-4-thiazolyl)-2-[[1-[[[[3-[[(1,4-dihydro-4-oxo-5-hydroxy-2-pyridinyl)-carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid 1,1-dimethylethyl ester potassium salt; or 2-[[[1-(2-amino-4-thiazolyl)-2-[[1-[[[[3-[[(1,4-dihydro-4-oxo-5-hydroxy-2-pyridinyl)carbonyl]amino]-2,5-dioxo-1-imidazolidinyl]sulfonyl]amino]carbonyl]-2-oxo-3-azetidinyl]amino]-2-oxoethylidene]amino]oxy]-2-methyl propanoic acid.

6. A compound of claim 3; wherein $R_{100}$ is a heterocyclic compound of Formula 4 and wherein M is carbonyl.

7. A compound of claim 3; wherein $R_{100}$ is a heterocyclic compound of Formula 4 and wherein M is methylene.

8. A compound of claim 6; wherein Z is NH.

9. A compound of claim 7; wherein Z is $C(R_{143})(R_{144})$; wherein $R_{143}$ and $R_{144}$ are hydrogen.

10. A compound of claim 8 which is Propanoic acid, 2-[[[1-(2-amino-4-thiazolyl)-2-[[1-[[[[1-[(1,4-dihydro-5-hydroxy-4-oxo-2-pyridinyl)carbonyl]tetrahydro-3-oxo-1,2,4-triazin-4(1H)-yl]sulfonyl]amino]carbonyl]-2-oxo-3-azetidinyl]amino]-2-oxoethylidene]amino]oxy]-2-methyl -, [S-(Z)]-.

11. A compound of claim 7 which is Acetic acid, 2-[[[1-(2-amino-4-thiazolyl) -2-[[1-[[[[4-[(1,4-dihydro-5-hydroxy-4-oxo-2-pyridinyl)-carbonyl]-1-piperazinyl]-sulfonyl]amino]carbonyl]-2-oxo-3-azetidinyl]amino]-2-oxoethylidene]amino]oxy]-, [S-(Z)]-.

12. A compound of claim 6 which is Propanoic acid, 2-[[[1-(2-amino-4-thiazolyl)-2-[[1-[[[[4-[(1,4-dihydro-5--hydroxy-4-oxo-2-pyridinyl)-carbonyl]-2-oxo-1-piperazinyl]sulfonyl]amino]carbonyl]-2-oxo-3-azetidinyl]amino]-2-oxoethylidene]amino]oxy]-2-methyl-, [S-(Z)]-.

13. A compound of claim 3; wherein $R_{100}$ is a heterocyclic compound of Formula 5; wherein $R_{151}$ and $R_{152}$ are hydrogen.

14. A compound of claim 3; wherein $R_{100}$ is a heterocyclic compound of Formula 5; wherein $R_{151}$ is methyl and $R_{152}$ is hydrogen.

15. A compound of claim 13 which is Propanoic acid, 2-[[[1-(2-amino-4-thiazolyl)-2-[[1-[[[[3-(1,4-dihydro--5-hydroxy-4-oxo-2-pyridinyl)-2,5-dihydro-5-oxo-1H-1,2,4-triazolyl-1-yl]sulfonyl]amino]carbonyl]-2-oxo-3-azetidinyl]amino]-2-oxoethylidene]amino]oxy]-2-methyl-, [S-(Z)]-.

16. A compound of claim 14 which is Propanoic acid, 2-[[[1-(2-amino-4-thiazolyl)-2-[[1-[[[[3-(1,4-dihydro-5-hydroxy-4-oxo-2-pyridinyl)-4,5-dihydro-4-methyl-5-oxo-1H-1,2,4-triazolyl-1-yl]sulfonyl]amino]-carbonyl]-2-oxo-3-azetidinyl]amino]-2-oxoethylidene]amino]oxy]-2-methyl-, [S-(Z)]-.

17. A compound of claim 3; wherein $R_{100}$ is a heterocyclic compound of Formula 3; wherein $R_{131}$, $R_{132}$, $R_{133}$, $R_{134}$ and $R_{135}$ are hydrogen.

18. A compound of claim 17 which is [[1-(α-[[-1-[[[[4-[[(1,4-dihydro-5-hydroxy 4-oxo-2-pyridinyl)-carbonyl]amino]-[2-oxo-5-oxazolidinyl]methyl]sulfonyl]amino]carbonyl]-2-oxo-3-azetidinyl]amino]-2-[2-[[1,1-dimethylethoxy)carbonyl]amino]-4-thiazolyl]-2-oxoethylidene]amino]oxy]acetic acid 1,1-dimethylethyl ester; [[[1-(2-amino-4-thiazolyl)-2-[[1-[[[[4-[[(1,4-dihydro-5-hydroxy-4-oxo-2-pyridinyl)carbonyl]amino]-[2-oxo-5-oxazolydinyl]methyl]sulfonyl]amino]carbonyl]-2-oxo-3-azetidinyl]amino]-2 oxoethylidene]amino]oxy] acetic acid; 2-[[[2-[[1-[[[[4-[[(1,4-dihydro-5-hydroxy-4-oxo-2-pyridinyl)carbonyl]-amino]-[2-oxo-5-oxazolidinyl]methyl]sulfonyl]amino]carbonyl]-2-oxo-3acetidinyl]amino -1-[2-[[(1,1-dimethylethoxy)carbonyl]amino]-4-thiazolyl]- 2-oxoethylidene]amino]oxy]-2-methyl propanoic acid 1,1-dimethylethyl ester; or 2-[[[1-(2-amino-4-thiazolyl)-2-[[1-[[[[4-[[(1,4-dihydro-5-hydroxy-4-oxo-2-pyridinyl)carbonyl]amino]-[2-oxo-5-oxazolidinyl]methyl]sulfonyl]amino]carbonyl]-2-oxo-3-azetidinyl]-amino]-2-oxoethylidene]amino]oxy]-2-methyl propanoic acid.

19. A compound of claim 3; wherein $R_{160}$ is a pyridone of Formula 8, 9 or 10.

20. A compound of claim 19 which is Propanoic acid, 2-[[[1-(2-amino-4-thiazolyl)-2-[[1-[[[[3-[[(1,2-dihydro-1-hydroxy-2-oxo-4-pyridinyl)carbonyl]amino]-2-oxo-1-imidazolidinyl]sulfonyl]amino]carbonyl]-2-oxo-3-azetidinyl]-amino]-2-oxoethylidene]amino]oxy]-2-methyl-, [S-(Z)]-; Propanoic acid, 2-[[[1-(2-amino-4-thiazolyl)-2-[[1-[[[[3-[[(1,2-dihydro-1-hydroxy-2-oxo-5-pyridinyl)carbonyl]amino]-2-oxo-1-imidazolidinyl]sulfonyl]amino]carbonyl]-2-oxo-3-azetidinyl]-amino]-2-oxoethylidene]amino]oxy]-2-methyl-, [S-(Z)]-; Propanoic acid, 2-[[[2-[[1-(2-amino-4-thiazolyl)-2-[[1-[[[[3-[[(1,2-dihydro-1-hydroxy-2-oxo-6-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methyl-, [S-(Z)]-.

21. A compound of claim 3; wherein $R_{160}$ is a pyridone of Formula 6, wherein $L_1$ is methyl, butyl or cyclopropyl.

22. A compound of claim 21 which is Propanoic acid, 2-[[[1-(2-amino-4-thiazolyl)-2-[[1-[[[[3-[[(1-cyclopropyl-1,4-dihydro-5-hydroxy-4-oxo-3-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methyl-, [S-(Z)]-; Propanoic acid, 2-[[[1-(2-amino-4-thiazolyl)-2-[[1-[[[[3-[[(1,4-dihydro-5-hydroxy-1-methyl-4-oxo-2-pyridinyl)carbonyl]amino]-2-oxo-1-imidazolidinyl]sulfonyl]amino]carbonyl]-2-oxo-3-azetidinyl]amino]-2 oxoethylidene]amino]oxy]-2-methyl-, [S-(Z)]-; or Propanoic acid, 2-[[[1-(2-amino-4-thiazolyl)-2-[[1-[[[[3-[[(1-butyl-1,4-dihydro-5-hydroxy 4-oxo-2-pyridinyl)carbonyl]amino]-2-oxo-1-imidazolidinyl]sulfonyl]amino]carbonyl]-2-oxo-3-azetidinyl]amino]-2-oxoethylidene]amino]oxy]-2-methyl-, [S-(Z)]-.

23. A compound of claim 3; wherein $R_{160}$ is a pyridone of Formula 7.

24. A compound of claim 3 which is Acetic acid, [[[1-(2-amino-4-thiazolyl)-2-[[1-[[[[3-[[(1,4-dihydro-3-hydroxy-4-oxo-2-pyridinyl)-carbonyl]amino]-2-oxo-1-imidazolidinyl]sulfonyl]amino]carbonyl]-2-oxo-3-azetidinyl]amino]-2-oxoethylidene]amino]-oxy]-, [S-(Z)]-.

* * * * *